(12) United States Patent
Christgau et al.

(10) Patent No.: US 7,589,235 B2
(45) Date of Patent: Sep. 15, 2009

(54) HIGH YIELD AND RAPID SYNTHESIS METHODS FOR PRODUCING METALLO-ORGANIC SALTS

(75) Inventors: Stephan Christgau, Gentofte (DK); Jens E. T. Andersen, Vedbaek (DK)

(73) Assignee: Osteologix, A/S, Copenhagen (DK)

( * ) Notice: Subject to any disclaimer, the term of this patent is extended or adjusted under 35 U.S.C. 154(b) by 0 days.

(21) Appl. No.: 11/579,773

(22) PCT Filed: May 5, 2005

(86) PCT No.: PCT/DK2005/000307

§ 371 (c)(1),
(2), (4) Date: Jul. 23, 2007

(87) PCT Pub. No.: WO2005/108339

PCT Pub. Date: Nov. 17, 2005

(65) Prior Publication Data

US 2007/0282127 A1 Dec. 6, 2007

(30) Foreign Application Priority Data

| May 6, 2004 | (DK) | PCT/DK2004/000326 |
| May 6, 2004 | (DK) | PCT/DK2004/000327 |
| May 6, 2004 | (DK) | PCT/DK2004/000328 |
| Nov. 5, 2004 | (DK) | 2004 01708 |

(51) Int. Cl.
C07C 55/07 (2006.01)
C07C 55/08 (2006.01)
C07C 55/10 (2006.01)
C07C 55/12 (2006.01)
C07C 55/14 (2006.01)
C07C 55/16 (2006.01)
C07C 55/18 (2006.01)
C07C 55/20 (2006.01)
C07C 55/21 (2006.01)

(52) U.S. Cl. ............... 562/590; 562/568; 562/571; 562/573; 562/582; 562/584; 562/585; 562/597

(58) Field of Classification Search ............ None
See application file for complete search history.

(56) References Cited

U.S. PATENT DOCUMENTS

| 3,478,073 A | 11/1969 | Rydh |
| 4,056,567 A | 11/1977 | Lamberti et al. |
| 4,921,971 A * | 5/1990 | Krimmer et al. ............ 548/534 |
| 5,856,356 A * | 1/1999 | Tsouderos et al. .......... 514/492 |
| 6,207,335 B1 * | 3/2001 | Michel et al. ............... 430/114 |
| 6,232,497 B1 * | 5/2001 | Pischel ....................... 562/577 |
| 7,241,460 B2 * | 7/2007 | Jellum et al. ................ 424/601 |
| 2004/0063972 A1 | 4/2004 | Vaysee-Ludot et al. |
| 2006/0122274 A1 * | 6/2006 | Hansen et al. ............... 514/566 |
| 2006/0216358 A1 | 9/2006 | Hansen et al. |
| 2006/0275503 A1 | 12/2006 | Hansen et al. |

FOREIGN PATENT DOCUMENTS

| EP | 415850 | 6/1991 |
| FR | 2665896 A1 * | 2/1992 |
| GB | 729376 | 5/1995 |
| WO | WO 00/01692 | 1/2004 |
| WO | WO 2004/098617 | 11/2004 |
| WO | WO 2004/098618 | 11/2004 |
| WO | WO 2004/098619 | 11/2004 |
| WO | WO 2006/089546 | 8/2005 |
| WO | WO 2005/082385 | 9/2005 |
| WO | WO 2005/123192 | 12/2005 |
| WO | WO 2005/123193 | 12/2005 |
| WO | WO 2007/003200 | 1/2007 |

OTHER PUBLICATIONS

U.S. Appl. No. 11/994,695, filed Jul. 5, 2006, Christgau, Preliminary Amendment).
U.S. Appl. No. 10/590,892, filed Feb. 28, 2005, Hansen et al.
U.S. Appl. No. 11/629,613, filed Jun. 17, 2005, Christgau et al.
U.S. Appl. No. 11/629,612, filed Jun. 17, 2005, Christgau et al.
U.S. Appl. No. 11/817,181, filed Nov. 7, 2005, Christgau.
Bacce, E.D. et al., 2001, "Thermal decomposition and rehydration of strontium oxalate: morphoplogical evalution," Intl. Journal of Inorganic Materials, vol. 3, pp. 443-452.
Briggman B & Oskasson, 1977, Acta Cryst. B33; 1900-1906.
Schmidbaur H. et al., 1989, Chem. Ber. 122:1433-1438.
Schmidbaur et al. 1990, Chem Ber. 123:1599-1602.
Intl. Search Report for PCT application No. PCT/DK2005/00307; dated Nov. 24, 2005.

* cited by examiner

*Primary Examiner*—Brian J Davis
(74) *Attorney, Agent, or Firm*—Jones Day

(57) ABSTRACT

A new method for preparing salts of metal cations and organic acids, especially divalent salts of alkaline earth metal ions from group II of the periodic system and carboxylic acids. The method comprising the use of a high temperature (about 90° or more) and, optionally. high pressure, in order to obtain a higher yield, purity and faster reaction speed than obtained with known synthesis methods. In particular, the present invention relates to the production of strontium salts of carboxylic acids. Novel strontium salts are also provided by the present method.

26 Claims, 8 Drawing Sheets

HIGH YIELD AND RAPID SYNTHESIS METHODS FOR PRODUCING METALLO-ORGANIC SALTS

FIELD OF THE INVENTION

The present invention relates to methods of producing salts of metal cations and organic acids, especially salts of alkaline earth metal ions from group II of the periodic system and carboxylic acids. In particular, the present invention relates to the production of strontium salts of carboxylic acids. New procedures and conditions for performing such synthesis with higher purity, higher yields and with shorter processing times, than has previously been possible are described in the invention. Novel strontium salts are also provided by the present method.

BACKGROUND OF THE INVENTION

Alkaline earth metals and alkali metals are almost invariably found in an oxidized state as a component of metallo-organic salts due to the highly reactive nature of such elements. Salts of such metal-ions are widely distributed throughout nature. The distribution and relative abundance of various metal ions varies greatly, from very common elements such as calcium, magnesium, potassium and sodium to less common elements such as strontium, barium, lanthanum and gallium and very rare elements such as rubidium, caesium and beryllium.

Salts of alkaline earth metal and alkali metal compounds are used in a great number of industrial processes and in production of food products, medical products, pharmaceutical ingredients, vitamins and other health related products, products for personal care, as well as for a number of industrial products such as fertilizers, building materials, glass, iron and steel manufacture and in a great number of other products. Thus, efficient manufacture of pure metallo-organic salts is of enormous commercial interest.

For many of the practical uses of alkaline earth metals, specific salts must be manufactured, which possess the properties required for the desired application. Of particular interest for the present invention are situations where the metal-ion salts must be manufactured with high purity and with organic counter-ions not found in nature. Manufacture of such salts is generally made by various aqueous processes and it is in general difficult to control the homogeneity and purity of the reaction products necessitating re-crystallizations and other purification steps, which in turn results in low yields of the desired salt as appears from Briggman B & Oskasson (1977), Schmidbaur H et al. (1989) and Schmidbaur et al. (1990).

SUMMARY OF THE INVENTION

In one aspect, the invention relates to a method for the preparation of an alkaline earth metal and/or another divalent metal ion salt of an organic acid, the method comprising reacting at least one of a hydroxide and/or a halogen salt of the metal ion with the organic acid (anion) in an aqueous medium at a temperature of about 90° C. or more such as, e.g., about 100° C. or more, 120° C. or more, or about 125° C. or more for a time period of at the most about 60 min such as, e.g. at the most about 30 min or at the most about 20 min such as about 15 min.

In one embodiment of this method, the salt is formed between an organic acid containing at least one carboxylic acid group and an alkaline earth metal selected from the group comprising strontium, calcium and magnesium.

In some embodiments of the method, the alkaline earth metal is strontium. In some embodiments of the method, the organic acid is a mono-, di-, tri- or tetra-carboxylic acid.

In some embodiments of the method, the organic acid is selected from the group comprising: acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, phthalic acid, carbonic acid, formic acid, methanesulfonic acid, ethanesulfonic acid, camphoric acid, gluconic acid, L- and D-glutamic acid, pyruvic acid, L- and D-aspartic acid, trifluoroacetic acid, ranelic acid, 2,3,5,6-tetrabromobenzoic acid, 2,3,5,6-tetrachlorobenzoic acid, 2,3,6-tribromobenzoic acid, 2,3,6-trichlorobenzoic acid, 2,4-dichlorobenzoic acid, 2,4-dihydroxybenzoic acid, 2,6-dinitrobenzoic acid, 3,4-dimethoxybenzoic acid, abietic acid, acetoacetic acid, acetonedicarboxylic acid, aconitic acid, acrylic acid, adipic acid, alpha-ketoglutaric acid, anthranilic acid, benzilic acid, arachidic acid, azelaic acid, behenic acid, benzenesulfonic acid, beta-hydroxybutyric acid, brassidic acid, capric acid, chloroacrylic acid, cinnamic acid, citraconic acid, crotonic acid, cyclopentane-1,2-dicarboxylic acid, cyclopentane carboxylic acid, cystathionine, decanoic acid, erucic acid, ethylenediaminetetraacetic acid, fulvic acid, fumaric acid, gallic acid, glutaconic acid, glutaric acid, gulonic acid, glucosamine sulphate, heptanoic acid, hexanoic acid, humic acid, hydroxystearic acid, isophthalic acid, itaconic acid, lanthionine, lauric acid (dodecanoic acid), levulinic acid, linoleic acid (cis, cis-9,12-octadecadienoic acid), malic acid, m-chlorobenzoic acid, melissic acid, mesaconic acid, methacrylic acid, monochloroacetic acid, myristic acid, (tetradecanoic acid), nonanoic acid, norvaline, octanoic acid, oleic acid (cis-9-octadecenoic acid), ornithine, oxaloacetic acid, palmitic acid (hexadecanoic acid), p-aminobenzoic acid, p-chlorobenzoic acid, petroselic acid, phenylacetic acid, p-hydroxybenzoic acid, pimelic acid, propiolic acid, propionic acid, p-tert-butylbenzoic acid, p-toluenesulfonic acid, pyruvic acid, sarcosine, sebacic acid, serine, sorbic acid, stearic acid (octadecanoic acid), suberic acid, succinic acid, terephthalic acid, tetrolic acid, threonine, L-threonate, thyronine, tricarballylic acid, trichloroacetic acid, trimellitic acid, trimesic acid, tyrosine, ulmic acid and cylohexane carboxylic acid.

In some embodiments of the method, the organic acid is an amino carboxylic acid such as, e.g., a natural or synthetic amino acid. For example, n certain embodiments, the salt is selected from the group consisting of strontium glutamate, strontium aspartate, strontium malonate, strontium D-glutamate, strontium L-glutamate, strontium (L-)diglutamate pentahydrate, strontium D-aspartate, strontium L-aspartate, strontium maleate, strontium ascorbate, strontium threonate, strontium lactate, strontium pyruvate, strontium fumarate and strontium succinate. In specific embodiments, the salt is strontium malonate.

In some embodiments of the method, the molar ratio between the metal ion and the organic acid is in the range from 0.8:1 to 1.2:1, preferably above 1.05:1, such as above 1.1:1.

In specific embodiments of the method, the halogen salt is a chloride salt.

In some embodiments of the method, the reaction is performed in a closed container at a temperature of 100° C. or more and a pressure of 1 bar or more.

In certain embodiments of the method, the yield of the divalent metal salt is 70% or more such as, e.g., about 75% or more, about 80% or more, about 85% or more, about 90% or more or about 95% or more.

In some embodiments of the method, the amount of precipitated carbonate is less than 1%, such as less than 0.5% or less than 0.2% of the amount of divalent metal salt.

In some embodiments of the method, the method comprises, in addition to a divalent metal ion, a pharmaceutically active component containing an acid and/or amino group. In certain embodiments, the pharmaceutically active component is selected from the group consisting of Non Steroidal anti inflammatory agents (NSAIDs), Cyclo-oxygenase-2 (COX-2) inhibitors, COX-3 inhibitors, inducible nitric oxide synthetase (iNOS) inhibitors, PAR2 receptor antagonists, neuroleptic agents, opioids, Cyclooxygenase (COX)-inhibiting nitric oxide donators (CINOD), Disease modifying anti-rheumatic drugs (DMARD), bisphosphonates, N-acetylcholine receptor agonists, glycine antagonists, vanilloid receptor antagonists, neurokinin antagonists, N-Methyl-D-Aspartate (NMDA) receptor antagonists, calcitonin gene-related peptide antagonists and 6-(5-carboxy methyl-hexyloxy)-2,2-dimethyl-hexanoic acid and analogues thereof including active metabolites thereof.

In certain embodiments, the pharmaceutically active component is an NSAID selected from the group consisting of piroxicam, diclofenac, propionic acids including naproxen, flurbiprofen, fenoprofen, ketoprofen and ibuprofen, fenamates including mefenamic acid, paracetamol, indomethacin, sulindac, meloxicam, apazone, pyrazolones including phenylbutazone, salicylates including aspirin.

In certain embodiments, the pharmaceutically active component is selected from the group comprising is an inhibitor of the cyclooxygenase 2 enzyme (COX-2 inhibitor) with an inhibition constant below Ki 10 pm such as the following compounds: rofecoxib (Vioxx), valdecoxib (Bextra), celecoxib (Celebrex), etoricoxib (Arcoxia), lumiracoxib (Prexige), parecoxib (Dynastat), deracoxib (Deram), tiracoxib, meloxicam, nimesolide, (1,1-dimethylheptyl)-6 a, 7,10,10a-tetrahydro-1-hydroxy-6,6-dimethyl-6H-dibenzo[b,d]pyran carboxylic acid (CT-3); 2 (5H)-Furanone, 5,5-dimethyl(1-methylethoxy) [4(methylsulfonyl) phenyl]-(DFP); Carprofen (RIMADYLO); (Acetyloxy)-benzoic acid, 3-[(nitrooxy)-methyl]phenyl ester (NCX4016); P54 (CAS Reg. No. 1309960) 2,6-Bis(1,1-dimethylethyl) [(E)-(2-ethyl-1,1-dioxo isothiazolidinylidene)-methyl] phenol (S-2474); 5(R)-Thio sulfonamide-3 (2H)-benzofuranone (SVT-2016) and N-[3-(Formyl-amino) phenoxy-4H benzopyran yl]methane-sulfonamide ("T-614") and liclofelone [2,2-dimethyl-6-(4-chlorophenyl)-7-phenyl-2,3, dihydro-1H-pyrrolizine-5-yl]-acetic acid, as well as any pharmaceutically active derivatives and pharmaceutically acceptable salts thereof.

In certain embodiments, the pharmaceutically active component is an inhibitor of inducible NOS (iNOS) selected from the group consisting of amino-guanidine, $N^G$-Nitro-L-arginine, $N^G$-Monomethyl-L-arginine, $N^G$-(1-Iminoethyl)-L-lysine, $N^G$-Nitro-L-arginine, S-Methyl-L-thiocitrulline, $N^G$-Monomethyl-L-arginine acetate, diphenyleneiodonium chloride, isothiourea derivatives such as S-Methylisothiourea~, S-Ethylisothiourea, S-Isopropylisothiourea, and S-(2-Aminoethyl)-isothiourea, Monomethyl-L-arginine acetate, 2-iminopiperidine; 2,4-Dia-nino-6-hydroxy-pyrimidine; 5-chloro-1,3-dihydro-2H-benzimidazol-2-one (FR038251), 1,3(2H, 4H)-isoquinoline-dione (FR038470) and 5-chloro-2, 4(1H, 3H)-quinazolonedione (FR191863).

In certain embodiments, the pharmaceutically active component is a DMARD selected from the group comprising Doxycycline, Chondroitin Sulfate, Methotrexate, Leflounomide (ARAVA®, Aventis), Dimethylnitrosamine, azatriopine, hydroxychloroqine, cyclosporine, minocycline, salazopyrine, penicillamine, aurothiomalate (gold salt), cyclophosphamide, and azathioprine.

In certain embodiments, the pharmaceutically active component is a bisphosphonate selected from the group consisting of ibandronate, zoledronate, alendronate, risedronate, ethidronate, chlodronate, tiludronate, minodronate, incadronate, olpadronate and pamidronate.

In some embodiments of the method wherein the alkaline earth metal is strontium, the method comprises reacting strontium hydroxide with a di-carboxylic acid at a temperature in a range of from about 120° C. to about 135° C. and at a pressure of from about 1 to about 1.7 bar for a time period of from about 15 min to about 60 min to obtain a strontium salt of the employed dicarboxylic acid. The method can further comprise a step of filtering the hot reaction mixture immediately after heating is stopped to remove precipitated strontium carbonate from the reaction mixture.

In certain embodiments of the method precipitation of the strontium salt from the reaction mixture is improved by the addition of 5-60 vol/vol % alcohol, such as 5-40 vol/vol % alcohol or more preferred 10-25 vol/vol % alcohol to the solution. In a specific embodiment, the alcohol is ethanol. In another specific embodiment, the alcohol is methanol.

In another aspect, the invention relates to a strontium salt, which is strontium (L-) diglutamate pentahydrate. In some embodiments, the strontium salt has a crystal composition as shown in FIGS. 3 and/or 4 herein, and/or geometric properties as shown in Table 4, 5 and/or 6 herein. The strontium salt may be, for instance, for use in medicine.

In another aspect, the invention relates to a strontium salt, which is strontium D-glutamate hexahydrate. In some embodiments, the strontium salt has a crystal composition as shown in FIG. 7 herein and/or geometric properties as shown in Table 8 and/or 9. The strontium salt may be, for instance, for use in medicine.

DETAILED DESCRIPTION OF THE INVENTION

Figure 1:
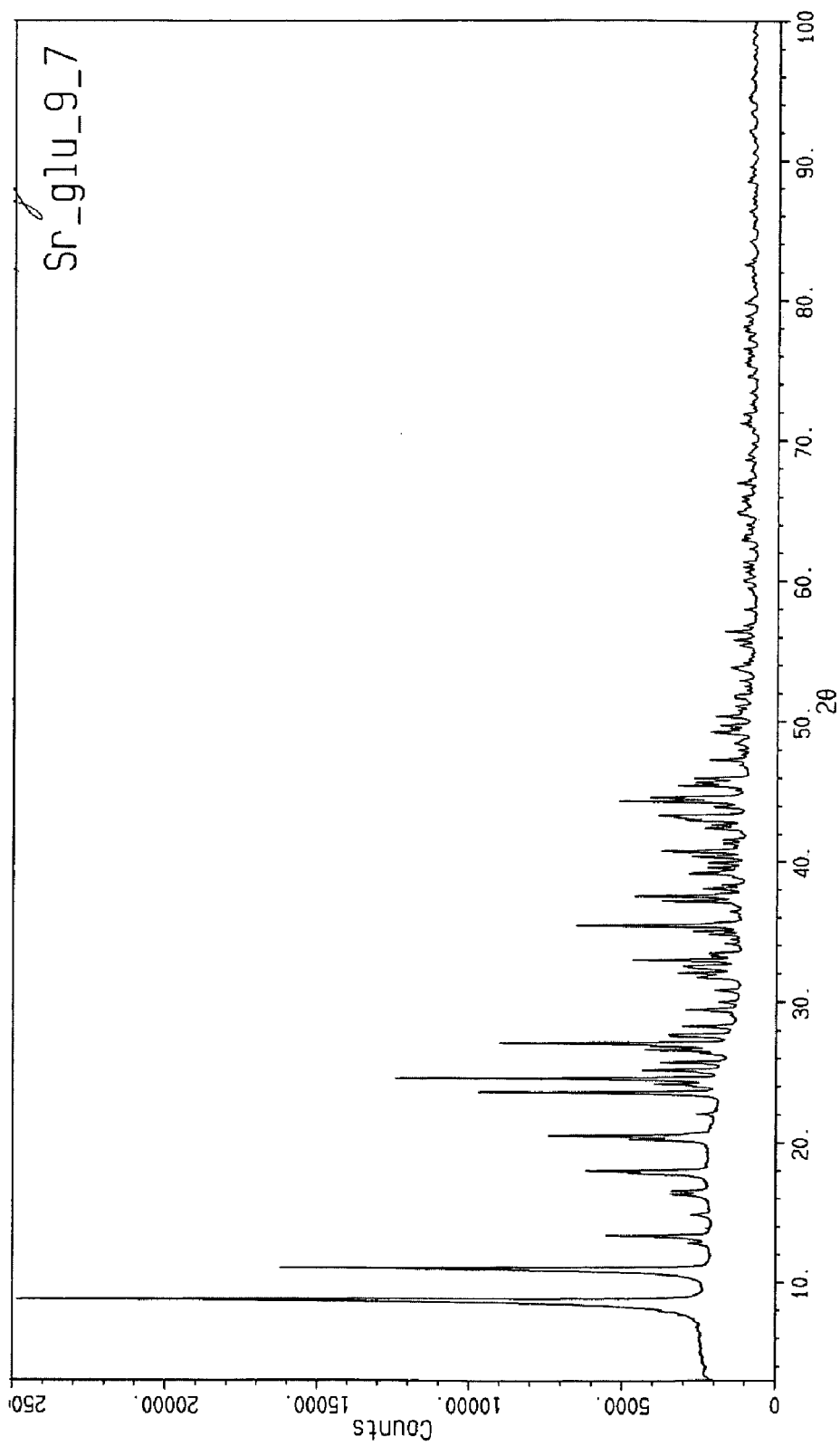
FIG. 1 shows diffractograms of the x-ray analysis of two strontium salts. The top diffractogram shows: Strontium glutamate hexahydrate, as synthesised by strontium hydroxide and L-glutamic acid at high temperature but using the reaction conditions described in example 2. This salt and the resulting diffractogram corresponds to the strontium L-glutamate hexahydrate salt previously described (H. Schmidbaur, I. Bach, L. Wilkinson & G. Müller (1989), Chem. Ber. 122; 1433-1438). The lower diffractogram shows a strontium glutamate hexahydrate salt synthesized from strontium chloride and L-glutamic acid as disclosed in the present example. The new strontium glutamate salt has been identified as strontium di-L-glutamate pentahydrate comprised of one strontium ion and two mono-protonated glutamate ions.
Figure 1:
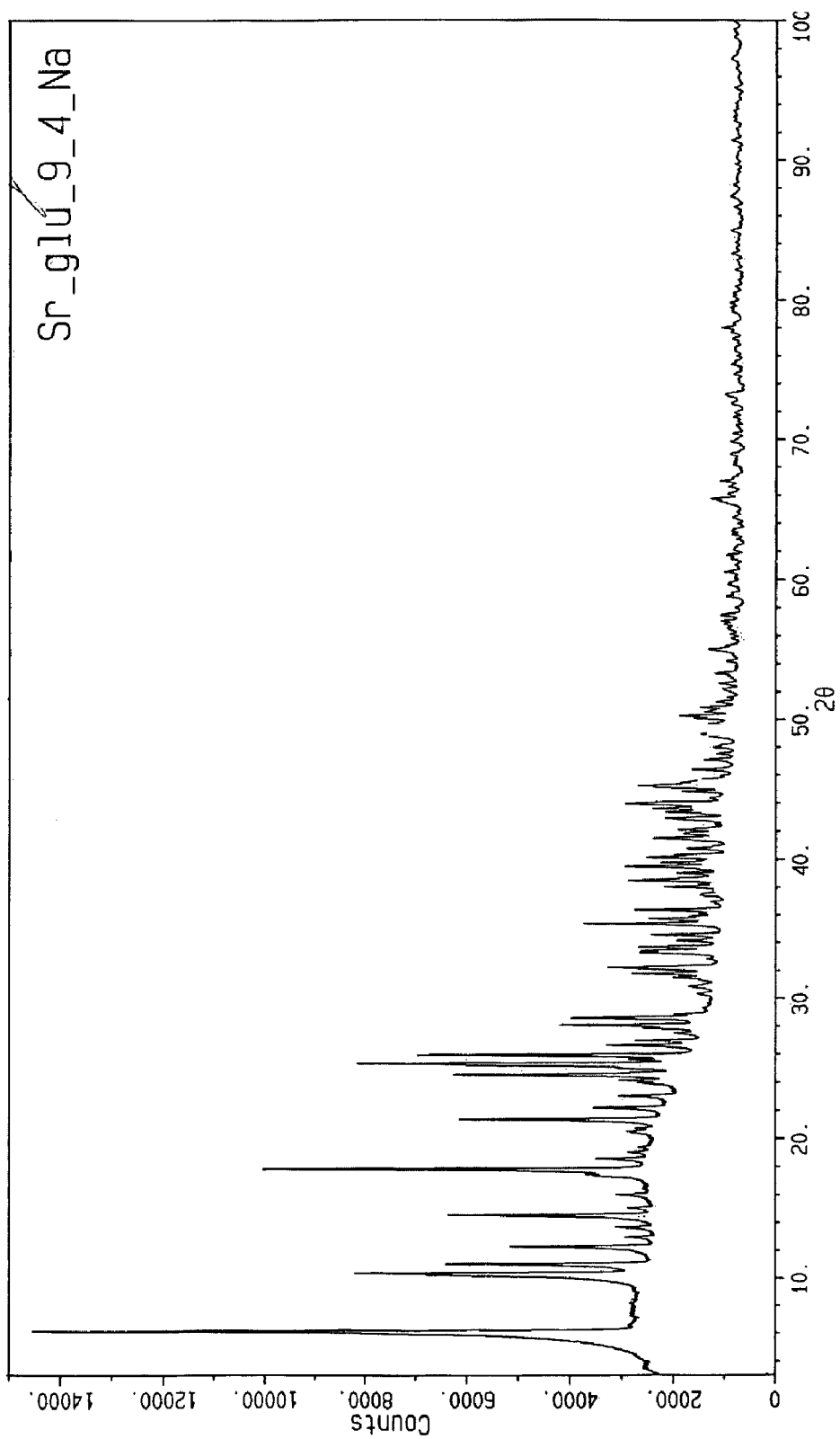

The present invention discloses a new method for synthesis and isolation of organic salts of metal-ions, especially of alkaline earth metals. In the manufacture method according to the invention a high temperature and, optionally, pressure is employed to ensure higher yield, purity and reaction speed than obtained with currently known synthesis methods for manufacture of organic salts of alkaline earth metals and alkali metals.

Accordingly, the present invention relates to a method for the preparation of a metal salt of all organic acid, the method comprising reacting a hydroxide or a halogen salt of the metal ion with the organic acid (anion) in an aqueous medium at a temperature of about 90° C. or more such as, e.g., about 100° C. or more, 120° C. or more, or about 125° C. or more for a time period of at the most about 60 min such as, e.g. at the most about 30 min or at the most about 20 min such as about 15 min.

In a specific embodiment the reaction may be performed in a closed container at a temperature of 100° C. or more and a pressure of 1 bar or more.

Examples are provided herein demonstrating the importance of reaction temperature and giving guidelines for establishing the optimum temperature for a given organo-metallic salt synthesis in particular for the synthesis of strontium salts. The synthesis allows production of some entirely new salts, where time, temperature and pressure are key parameters of compound purity. The synthesis method is applicable for the manufacture of most organic salts of metal ions, but in particular carboxylic acid salts of alkaline earth metals can be made according to the present invention with higher yield and purity than obtainable by other methods.

A crucial point in the method according to the invention is the avoidance of formation of relatively large amounts of insoluble carbonate. In fact, this is very difficult to avoid as the carbonate salts have very poor solubility and when formed rapidly precipitate from solution thereby contaminating the desired reaction products. Furthermore, the starting materials for synthesis of metallo-organic salts comprise a metal hydroxide or a metal halogenid (which enable conditions that are favorable for carbonate formation in an aqueous medium). If the organic acid of the metallo-organic salt is a carboxylic acid, which often be the case, it is generally realized that only gentle heating to slightly higher temperatures than room temperature can be accepted due to the risk of decarboxylation of the carboxylic acid and subsequent increase in the carbonate level.

Accordingly, the invention provides a method for the preparation of divalent metal salts that enables the use of a much higher reaction temperature than room temperature, a higher yield of the desired salt (as compared to the known methods) and at the same time keeps the formation of carbonate at a very low limit. The yield of the divalent metal salt prepared by a method according to the invention is 70% or more such as, e.g., about 75% or more, about 80% or more, about 85% or more, about 90% or more or about 95% or more. The amount of precipitated carbonate may be less than 1%, such as less than 0.75% or less than 0.5% or even below 0.2% of the amount of desired metallo-organo salt produced by the manufacturing process.

The method according to the invention may further comprise a step of filtering the hot reaction mixture immediately after heating is stopped to remove precipitated carbonate from the reaction mixture.

Furthermore, the present inventors have found that in order to accelerate the crystallization of the divalent metal salt, addition of small volumes of an alcohol such as, e.g., methanol or ethanol, such as from 5-10 vol/vol % to 50-60% vol/vol induces a significant acceleration of the precipitation of the desired salt. Addition of an alcohol is of special importance in the synthesis of salts with solubility exceeding 2 g/l at room temperature The production methods according to the invention are applicable for a wide range of different chemical substances. Of special relevance are applications where the desired metallo-organic salt is used in products for human use such as food-products, ingredients for pharmaceutical use, personal care products such as creams, lotions and toothpaste and vitamins and other nutritional supplements. In such cases, a high purity of the product is desired, and the manufacturing procedure described here provides a significant advantage compared to all other available methods.

A suitable metal for use in the method according to the invention is selected from metal atoms or ions, which have been tested for or are used for pharmaceutical purposes. Such metal atoms or ions belong to the group denoted alkaline metals, alkaline earth metals, light metals, transition metals, post transition metals or semi-metals (according to the periodic system).

Preferred metals are alkaline earth metals including beryllium, magnesium, calcium, strontium and barium and radium. The method is especially suitable for metals wherein the production of carbonate is problematic and unwanted.

As it appears from the examples herein, an especially suitable embodiment of the invention uses a chloride salt of the metal ion as a starting material. However, as it appears from the Examples herein metal hydroxides is also found to be well suited as starting a starting reagents for synthesis of metallo-organic salts.

The molar ratio between the metal ion and the organic acid is of importance in order to achieve the best possible yield. Normally, the molar ratio is at least about 0.8:1 such as about 1:1, preferably above 1.1:1 such as 1.2:1.

In principle, the organic acid may be any organic acid. In specific embodiments, the organic acid is a mono-, di-, tri- or quatro-carboxylic acid. Examples of suitable organic acids for use in a method according to the invention are e.g. acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, ibuprofenic acid, benzoic acid, salicylic acid, phthalic acid, carbonic acid, formic acid, methanesulfonic acid, ethanesulfonic acid, camphoric acid, gluconic acid, L- and D-glutamic acid, pyruvic acid, L- and D-aspartic acid, trifluoroacetic acid, ranelic acid, 2,3,5,6-tetrabromobenzoic acid, 2,3,5,6-tetrachlorobenzoic acid, 2,3,6-tribromobenzoic acid, 2,3,6-trichlorobenzoic acid, 2,4-dichlorobenzoic acid, 2,4-dihydroxybenzoic acid, 2,6-dinitrobenzoic acid, 3,4-dimethoxybenzoic acid, abietic acid, acetoacetic acid, acetonedicarboxylic acid, aconitic acid, acrylic acid, adipic acid, alpha-ketoglutaric acid, anthranilic acid, benzilic acid, arachidic acid, azelaic acid, behenic acid, benzenesulfonic acid, beta-hydroxybutyric acid, brassidic acid, capric acid, chloroacrylic acid, cinnamic acid, citraconic acid, crotonic acid, cyclopentane-1,2-dicarboxylic acid, cyclopentanecarboxylic acid, cystathionine, decanoic acid, erucic acid, ethylene-diaminetetraacetic acid, fulvic acid, fumaric acid, gallic acid, glutaconic acid, glutaric acid, gulonic acid, glucosamine sulphate, heptanoic acid, hexanoic acid, humic acid, hydroxystearic acid, isophthalic acid, itaconic acid, lanthionine, lauric acid (dodecanoic acid), levulinic acid, linoleic acid (cis, cis-9,12-octadecadienoic acid), malic acid, m-chlorobenzoic acid, melissic acid, mesaconic acid, methacrylic acid, monochloroacetic acid, myristic acid, (tetradecanoic acid), nonanoic acid, norvaline, octanoic acid, oleic acid (cis-9-octadecenoic acid), ornithine, oxaloacetic acid, palmitic acid (hexadecanoic acid), p-aminobenzoic acid, p-chlorobenzoic acid, petroselic acid, phenylacetic acid, p-hydroxybenzoic acid, pimelic acid, propiolic acid, propionic acid, p-tert-butylbenzoic acid, p-toluenesulfonic acid, pyruvic acid, sarcosine, sebacic acid, serine, sorbic acid, stearic acid (octadecanoic acid), suberic acid, succinic acid, terephthalic acid, tetrolic acid, threonine, L-threonate, thyronine, tricarballylic acid, trichloroacetic acid, trimellitic acid, trimesic acid, tyrosine, ulmic acid and cylohexanecarboxylic acid.

In specific embodiments, the organic acid is an amino carboxylic acid such as, e.g., a natural or synthetic amino acid.

Other divalent metal salts that may be prepared according to the present invention are comprised of a divalent metal ion and an anion selected from the group of pharmaceutically active compounds with an acid or amine group such as: salicylates such as acetyl salicylic acid, piroxicam, tenoxicam, ascorbic acid, nystatin, mesalazin, sulfasalazin, olsalazin, glutaminic acid, repaglinid, Methotrexate, Leflounomide, Dimethylnitrosamine, azatriopine, hydroxychloroqine, cyclosporine, minocycline, salazopyrine, penicillamine, diclofenac, propionic acids such as naproxen, flurbiprofen, fenoprofen, ketoprofen and ibuprofen, pyrazolones including phenylbutazone, fenamates such as mefenamic acid, indomethacin, sulindac, meloxicam, apazone, pyrazolones such as phenylbutazone, bisphosphonates such as zoledronic acid, minodronic acid, incadronic acid, ibandronate, alendronate, risedronate, olpadronate, chlodronate, tiludronate and pamidronate, COX-2 preferential cyclo-oxygenase inhibitors such as celecoxib, valdecoxib, etoricoxib, lumiracoxib, parecoxib, rofecoxib and deracoxib, pantotenic acid, epoprostenol, iloprost, tirofiban, tranexamic acid, folic acid, furosemide, bumetanide, kanrenoic acid, capopril, rasagiline, enalapril, lisinopril, ramipril, fosinopril, trandolapril, valsartan, telmisartan, pravastatin, fluvostatin, atorvastatin, cerivastatin, sulfadiazine, tretionin, adapalen, azelaic acid, dinoproston, levotyroxin, lityronin, doxycyclin, lymecyclin, oxytetracyclin, tetracycline, ampicilin, amoxicillin, clavulanic acid, taxobactam, nalidiksinic acid fusidinic acid and liclofelone [2,2-dimethyl-6-(4-chlorophenyl)-7-phenyl-2,3, dihydro-1H-pyrrolizine-5-yl]-acetic acid, as well as any pharmaceutically active derivative of the compounds.

Other examples of relevant acids for making strontium salts for use in a pharmaceutical composition may be found in WO 00/01692, which is hereby incorporated by reference.

The method according to the invention may be used to prepare a wide range of metal salts. In specific embodiments of the invention the metal salt may be formed between an organic acid containing at least one carboxylic acid functional group and an alkaline earth metal selected from the group comprising strontium, calcium and magnesium. Especially strontium is regarded as an interesting component in the treatment of various diseases, particularly diseases involving aberrant regulation of bone and/or cartilage metabolism (see the detailed discussion below) and, in a specific embodiment of the invention the metal is strontium.

To illustrate the potential of the method according to the present invention, a detailed description of its application for manufacture of organic strontium salts is provided. However, this is merely meant to illustrate the potential of the invention and not to limit the scope in any way.

Strontium

Strontium is found naturally exclusively as a non-radioactive stable element. Twenty-six isotopes of strontium have been described, but only stable non-radioactive strontium is found on earth. Natural strontium is a mixture of the 4 stable isotopes Sr-84, Sr-86, Sr-87, and Sr-88, of which the isotope Sr-88 is the most common comprising 82.5% of all stable strontium on earth. The average molar weight of natural non-radioactive strontium is 87.62 Da. Other known, non-natural, isotopes of strontium are radioactive, and of these radioactive strontium isotopes, Strontium-90 and Sr-89 are the most important. They are powerful beta-emitters with several commercial uses. Sr-89 is utilized in some medical applications, whereas Sr-90 finds it main use in auxiliary nuclear power devices for use in very special applications such as generating electric power to satellites and remote power stations. The medical use of Sr-89 is mainly related to the potential of strontium to target mineralized bone tissue where the radioactive Sr-89 isotope is employed to destroy bone tumors.

In nature, strontium is practically always found in the oxidized state as a di-cation and consequently is found as a salt, complexed with inorganic anions such as carbonate, sulphate and phosphate. A relatively limited number of strontium salts have been subjected to detailed chemical characterization, with full resolution of structure and chemical properties. Generally the strontium salts studied show properties similar to the corresponding salts of other second main group alkaline earth metals. This means that properties of a given strontium salt can be expected to mimic the corresponding calcium, magnesium and barium salts.

The naturally occurring salts of strontium, such as the carbonate and sulphate salts, have very low water solubility (0.15 g/l or below at room temperature). This solubility is lower than the corresponding calcium and magnesium salts, which is in accordance with the ionic and electropositive nature of strontium being greater than that of calcium. An important example of an exemption to the rule is found in the solubility of hydroxides where strontium hydroxide is the more soluble. Thus, the general observation is that the aqueous solubility of most inorganic strontium salts is lower than the analogous calcium salts. This is a result of the lower polarizing power of ionic strontium compared to calcium and magnesium ions, which have a higher polarizing power due to their smaller nuclear radii (0.99 Å for calcium compared with 1.12 Å for strontium). However, it must be emphasized that many inorganic strontium salts are highly soluble. As examples, strontium chloride, strontium hydroxide, strontium nitrate and strontium oxide are highly soluble with solubility in the range from 225-800 g/l in water. For some strontium salts, such as the hydroxide salt, the solubility is higher than the corresponding calcium or magnesium salts.

Organic strontium salts have been described, but literature reports of this type of compounds are limited to rather few substances. All these are strontium salts of anions containing carboxylic acids. The physiochemical properties of organic strontium salts have been reported to be similar to the corresponding magnesium, calcium and barium salts (Schmidbaur H et al. Chem. Ber. (1989) 122: 1433-1438). Strontium salts of carboxylic acids are crystalline non-volatile solids with strong electrostatic forces holding the ions in the crystal lattice. Most crystalline forms of organic strontium salts contain various amounts of crystal water, which serves to coordinate with the strontium ions in the crystal lattice. The temperature required for melting these salt are most often so high, that before it can be reached the carbon-carbon bonds of the organic anion breaks and the molecule decomposes, generally at a temperature of 300-400° C. (Schmidbaur H et al. Chem. Ber. (1989) 122: 1433-1438).

All alkaline earth metal salts of carboxylic acids are soluble to some extent in aqueous solutions, but the solubility of the specific salts vary considerably depending on the size and hydrophobicity as well as electrostatic properties of the organic anion. One of the simplest organic carboxylic acids, acetate, makes well-defined crystalline salts of strontium, which are highly soluble in water (solubility 369 g/l at room temperature). Larger organic anions usually have considerable lower solubility, depending on the hydration enthalpy and lattice enthalpy of the salt. However, as various strontium salts would not necessarily form the same type of crystal structure and their crystal lattice energies are unknown, it is not possible to make theoretical calculations of the solubility of such salts, but they will have to be determined empirically. Furthermore, a given salt may exist in different crystal structures, where important properties, such as the amount of bound crystal water varies, and thus different crystal forms will have different lattice and hydration enthalpies and thus solubility.

Properties of Carboxylic Acid Salts of Strontium

Carboxylic acids salts of divalent earth metals such as strontium, and especially di-carboxylic acids have some unique properties, as they can have a partial chelating effect in solution. In these cases the salt exists in solution as a complex in which the divalent metal ion is bound in a complex to the carboxylic groups of the anion. Such complexation may be important in biological systems, where the alkaline earth metals, especially calcium and magnesium, play vital physiological roles. A majority of divalent metal ions may exist in complex bound form in the aqueous environment in biological systems, rather than in a free and un-bound ionic form. Complex formation constants with the alkaline earth metals in aqueous solution are higher for amino acids than for hydroxy-carboxylic acids and the related non-carboxylic acids, which suggest that the amino group may play a role in the complex formation. Generally, the differences in association constants and hydration enthalpy for the various ligands become smaller as the radius of the metal increases. Thus, the stability of strontium complexes with di-carboxylic acid is lower than the stability of the comparable complexes with calcium and magnesium. This means that in aqueous solutions the chelating di-carboxylic acids will have a propensity to preferentially bind calcium and magnesium rather than the larger ions of strontium and barium.

Few organic strontium salts have found commercial applications, and thus no such compounds are available in large-scale chemical manufacture (>1000 kg batch size). However, recently, the strontium salt of the tetra-carboxylic acid, ranelate, has been developed for pharmaceutical use in treatment of metabolic bone diseases such as osteoporosis. The chemical properties of strontium ranelate are similar to many di-carboxylic acid salts of strontium. In water it has a solubility of 0.76 μl at 22-24° C., with slight increases in solubility at higher temperatures and lower pH. In aqueous solutions the ranelate ion functions as a chelator, complexing divalent metal ions as described above. The core 3-cyano-4-carboxymethylthiophene structure of the ranelate ion is chemically stable under physiological conditions, although the nitrile group may undergo hydrolysis to form various □-hydroxyacids or unsaturated acid derivatives of ranelate.

Synthesis of Carboxylic Acid Salts of Strontium

Organic-strontium salts of carboxylic acid anions can be synthesized by a number of different pathways. A conventional method for preparation of such organic strontium salts is to utilize the reaction between an organic acid and strontium hydroxide in an aqueous solution. As an example, the reaction scheme below shows this neutralization reaction of malonic acid and strontium hydroxide salt:

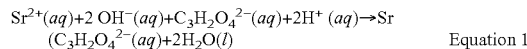

$$Sr^{2+}(aq)+2\ OH^-(aq)+C_3H_2O_4^{2-}(aq)+2H^+(aq) \rightarrow Sr(C_3H_2O_4^{2-})(aq)+2H_2O(l) \qquad \text{Equation 1}$$

After the reaction, which occurs rapidly upon dissolution of the solids, the suspension of dissolved strontium malonate can then be induced to precipitate by evaporation of water and subsequent up-concentration of the salt. Crystals of strontium malonate will slowly form and precipitate from the solution.

An alternative approach is to utilize the sodium or potassium salt of the appropriate carboxylic acid anion and strontium chloride. As all organic strontium salts will be less soluble than the highly soluble chloride salt, the organic strontium salt will precipitate under these conditions leaving NaCl and excess $SrCl_2$ in the solution. The equation below exemplifies this reaction scheme using as an example the reaction between $SrCl_2$ and sodium-malonate, where reaction products are added in equimolar amounts.

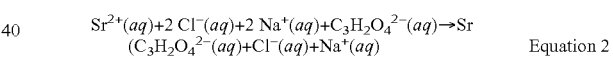

$$Sr^{2+}(aq)+2\ Cl^-(aq)+2\ Na^+(aq)+C_3H_2O_4^{2-}(aq) \rightarrow Sr(C_3H_2O_4^{2-})(aq)+Cl^-(aq)+Na^+(aq) \qquad \text{Equation 2}$$

In both the alternative synthesis pathways, re-crystallizations are likely to be required in order to obtain the desired strontium salt in sufficiently pure form. In turn the yield will decrease as a consequence of loss of material during re-crystallization owing to the lack of complete precipitation of strontium from solution and from formation of strontium carbonate that precipitate and due to the very low solubility of metal carbonates makes the precipitated strontium unavailable for further reaction. In alkaline solution, carbonate is formed by dissolution of atmospheric carbon dioxide, according to:

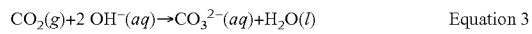

$$CO_2(g)+2\ OH^-(aq) \rightarrow CO_3^{2-}(aq)+H_2O(l) \qquad \text{Equation 3}$$

Since strontium carbonate is readily formed and has a low solubility product, Equation 3 is displaced towards the right, which extracts strontium from the product carboxylate, that is, Equation 1 (or 2) is displaced to the left. Thus, repetitive re-crystallisations will reduce the yield of the desired strontium carboxylate, while increase the presence of contaminating strontium carbonate.

The reaction schemes shown above (Equations 1 and 2) are depicting the final reaction for manufacture of organic strontium salts involving a simple reaction of an inorganic strontium salt with the desired organic anion in either free acid form or available as a salt. Thus, in order to carry out these reactions it is required that the organic acid is commercially available. In the case of more complex and/or unusual anions, they will have to be synthesized prior to the preparation of the strontium salt and formation of the strontium salt by reaction schemes as outlined above may then be incorporated in the last synthesis step. In either case the methods and procedures disclosed in the present patent may be of great use in improving the yields and purities of the desired reaction products According to the method of the present invention, manufacture of any strontium salt, or salt comprised of an organic anion and a metal cation such as e.g. an alkaline earth metal or alkali metal cation, especially an alkaline earth metal cation, may be synthesized more efficiently with higher yield, better purity and shorter processing times by performing the reactions at elevated temperature, under inert atmosphere and optionally with higher pressure. In specific the present inventors demonstrate a dramatic improvement in yield and purity of strontium salts produced in this way compared with previous synthesis methods disclosed in the prior art literature.

The present manufacturing method can be used for production of strontium salts of dicarboxylic organic anions, which may be used in the preparation of prophylactic and/or therapeutic treatments of metabolic bone diseases.

High strontium intake has in several animal studies been associated with alterations in bone mineralization and increased skeletal strength. The effect is believed to be due to a stimulatory effect of strontium on pre-osteoblastic cell maturation, migration and activity, and a direct or matrix-mediated inhibition of osteoclast activity by strontium. In other words, strontium both works as an anti-resorptive and an anabolic agent on bone tissue.

Various salts of strontium are known from the prior art, such as, e.g., strontium ranelate (distrontium salt of 2-[N,N-di(carboxymethyl)amino]-3-cyano-4-carboxymethyl-thiophene-5-carboxylic acid) described in EP-B 0 415 850. Other known strontium salts are e.g., strontium tartrate, strontium phosphate, strontium carbonate, strontium nitrate, strontium sulfate and strontium chloride. The present inventors have found that strontium salts of some dicarboxylic acids, such as strontium malonate, strontium fumarate, strontium succinate, strontium glutamate and strontium aspartate are more soluble than other dicarboxylic strontium salts of similar molecular size. In pure aqueous solutions of such salts, strontium exists in partly complexed form. When administered to an animal such as a mammal, i.e. a rat, dog, monkey or human, ionic strontium as well as strontium complexed to the carboxylic acid anion will be taken up from the intestinal lumen by both passive and active transport mechanisms. In this case strontium will be displaced from the complexes by available calcium and magnesium which forms much more stable complexes with the ionized amino acids. Certain dicarboxylic acids may be especially suited for prophylactic and/or therapeutic interventions in bone disease as they may act to preferentially bind/complex with available free calcium, thus promoting both the intestinal uptake of the calcium ion, and physiological action of the ion, in particular its role in regulation of bone turnover. Specific salts of interest are strontium salts formed with acids like fumaric acid, maleic acid, malonic acid, lactic acid, citric acid, tartaric acid, ascorbic acid, salicylic acid, acetyl-salicylic acid, pyruvic acid, L- and D-aspartic acid, gluconic acid, L- and D-glutamic acid, ranelic acid, alpha-ketoglutaric acid, arachidic acid, cyclopentane-1, 2-dicarboxylic acid, malic acid, myristic acid (tetradecanoic acid), pyruvic acid, sarcosine, serine, sorbic acid, threonine, thyronine and tyrosine.

In a specific embodiment the salts formed are strontium malonate, strontium lactate strontium succinate, strontium fumarate, strontium ascorbate in L and/or D-form, strontium aspartate in either L and/or D-form, strontium glutamate in either L- and/or D-form, strontium pyruvate, strontium tartrate, strontium threonate, strontium glutarate, strontium maleate, strontium methanesulfonate, strontium benzenesulfonate and mixtures thereof.

Novel strontium salts are also provided by the present invention such as strontium L-diglutamate pentahydrate and strontium D-glutamate hexahydrate. These salts are described below for the first time and the convenient manufacture in high purity of these previously undisclosed and/or difficult-to-manufacture alkaline earth metal salts of organic acids demonstrate the potentials of the disclosed manufacturing method for efficient synthesis of difficult organo-metallic salts.

Strontium Malonate

Strontium malonate has previously been described in the literature. However, synthesis methods for manufacture of strontium malonate in pure form have not previously been described in detail.

Figure 2:
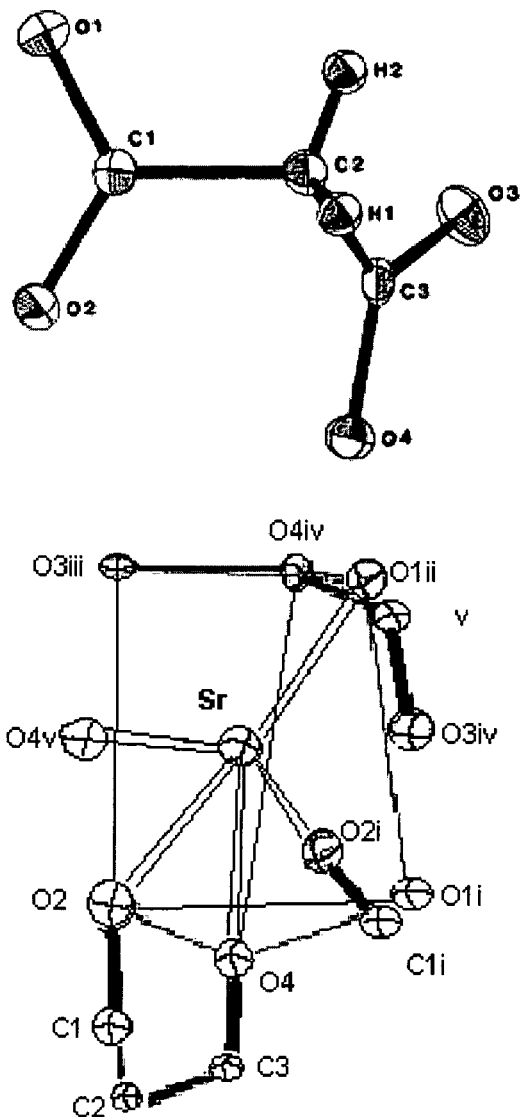
FIG. 2 shows the molecular structure of strontium malonate (anhydrous) in the crystalline form as disclosed by Briggman B & Oskasson Å 1977, Acta Cryst. B33; 1900-1906. The crystal is shown with atoms depicted with arbitrary radii.

In one report an anhydrous strontium malonate salt was described. The authors reported that slow evaporation at room temperature over several days of an aqueous solution of malonic acid and strontium hydroxide resulted in colorless single crystals. These crystals were analyzed by X-ray crystallography and shown to be orthorhombic unit cell with no crystal water bound (Briggman B & Oskasson A 1977, Acta Cryst. B33; 1900-1906). FIG. 2 and Table 1 below give a schematic presentation of the resolved crystal structure of the anhydrous strontium malonate salt:

TABLE 1

Distances [Å] and angles [°] for the malonate ion in the anhydrous crystalline form of strontium malonate as described by Briggman & Oskasson 1977. For atom nomenclature please refer to FIG. 2.

| Distances | | | |
|---|---|---|---|
| C(1)-C(2) | 1.529(5) | C(2)-H(1) | 1.04(5) |
| C(2)-C(3) | 1.525(5) | C(2)-H(2) | 0.89(5) |
| C(1)-O(1) | 1.262(4) | O(1)-O(2) | 2.505(3) |
| C(1)-O(2) | 1.252(4) | O(3)-O(4) | 2.207(3) |
| C(3)-O(3) | 1.250(4) | O(2)-O(4) | 2.924(3) |
| C(3)-O(4) | 1.270(4) | | |
| Angles | | | |
| C(1)-C2(2)-C(3) | 112.5(3) | C(2)-C(3)-O(3) | 119.3(3) |
| O(1)-C(1)-C(2) | 117.2(3) | C(2)-C(3)-O(4) | 118.4(3) |
| O(2)-C(1)-C(2) | 120.2(3) | O(3)-C(3)-O(4) | 122.4(3) |
| O(1)-C(1)-O(2) | 122.6(3) | H(1)-C(2)-H(2) | 113(4) |

At least two crystalline forms of strontium malonate exist, one anhydrous as described in FIG. 2 and Table 1 above and a form with one molecule of water pr. unit cell in the crystal. In situations where a high strontium content of the salt is desired, such as in pharmaceutical applications, the use of the anhydrous salt is preferred, as strontium constitutes 45.7% of the salt on a molar basis. Thus a manufacturing procedure that allows reproducible and controlled manufacture of this salt in high purity and yields is of great value.

In the synthesis of strontium malonate, the total yield of the product depends on temperature and on time of synthesis. Thus, the synthesis might be improved by testing the synthesis in an autoclave system, where the temperatures are maintained below the temperature of decomposition of the organic anion moiety of the desired strontium salt. As an example, malonic acid decomposes under neutral or acid conditions at 132-134° C., and thus synthesis of strontium malonate must be performed at temperatures below 132° C. However, alkaline conditions enhance the stability of malonate, which may enable synthesis at temperatures above the normal temperature of decomposition.

Of further relevance is the fact that carboxylates may decarboxylate upon heating (O) and release gaseous carbon dioxide. The reactions depicted in Equations 4 and 5 demonstrate that decarboxylation of malonic acid is facilitated by addition of acid that promotes the reaction through an intermediate of a carbanion:

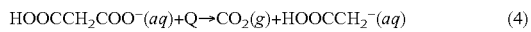
$$HOOCCH_2COO^-(aq) + Q \rightarrow CO_2(g) + HOOCCH_2^-(aq) \quad (4)$$

$$HOOCCH_2^-(aq) + H^+(aq) \rightarrow CH_3COOH(aq) \quad (5)$$

At low temperatures, the decarboxylation is not pronounced because the reaction of Equation 4 is slow. However, by elevating the temperature and adding acid, the reaction may proceed to completion. In the synthesis of strontium malonate, it was found by the optimization procedure that it could be produced in high yields by using sealed reaction vessels with a gas pressure of either an inert gas or steam under alkaline conditions. This result of the optimization complies with the reactions of Equations 4 and 5, which predict that they are both displaced to the left, thus favoring the stability of malonate ions. Steam and argon were used to lower the risk of decarboxylation, but other inert gases could be used as well.

Accordingly, strontium malonate may be synthesized by reacting a suspension of malonic acid with strontium hydroxide at a temperature maintained at or above 1000 but below 130° C. to avoid decomposition of malonic acid, and at an elevated pressure (at or above 1 bar) in a closed container. By this method a high yield of pure strontium malonate can be obtained after a reaction time of only 15 min, and a single filtration step.

Strontium Glutamate

Strontium L-glutamate has previously been prepared by reacting strontium hydroxide with L-glutamic acid under reflux for 3 hours with a subsequent cooling and slow crystallization over a period of up to 2 weeks.

In a method according to the present invention strontium L-glutamate hexahydrate has been prepared by reacting strontium hydroxide with glutamic acid at a temperature in a range of from about 120° C. to about 135° C. and at a pressure of from about 1 to about 1.7 bar, optionally under an inert gas atmosphere, for a time period of from about 15 min to about 60 min to obtain strontium glutamate. The method may further involve a step of filtering the hot reaction mixture immediately after heating is stopped to remove precipitated calcium carbonate from the reaction mixture. Further details and guidelines for optimization of the reaction appears from Example 8.

As mentioned above, by use of the method according to the present invention, the present inventors have prepared a new glutamate salt of strontium (strontium L-diglutamate pentahydrate) that is distinct from the known strontium glutamate.

Details concerning the preparation and crystal structure of this novel salt is found in Example 5 herein. In the following is given details with respect to this novel salt.

The X-ray crystalographic analysis (FIG. 1) revealed that the synthesized strontium glutamate salt was distinct from the previously described strontium L-glutamate hexahydrate salt described in FIGS. 1 and 2 and Tables 2 and 3.

Another novel strontium glutamate salt that has been produced by the method according to the present invention is strontium D-glutamate hexahydrate. The properties and crystal structure of this salt is described in Example 10.

Both in the case of strontium D-glutamate hexahydrate and strontium di-L-glutamate pentahydrate, the rapid production of these two novel organic salts of strontium in high purity and homogeneous crystalline formapplicable for X-ray analysis by the high temperature production method described in the present patent, provides an exemplification of the applicability of the method for producing difficult organo-metallic salts.

Strontium Aspartate

Strontium L-aspartate has also previously been prepared by reacting L-aspartic acid with strontium hydroxide. The reaction was performed over 3 hours under reflux, and the resulting reaction mixture was allowed to cool over three days to initiate crystal formation. The resulting strontium L-aspartate crystals were subjected to X-ray crystallography in order to elucidate the crystal structure (please see: H. Schmidbaur, P. Mikulcik & G. Müller (1990), Chem. Ber. 123; 1599-1602). The investigations revealed that the isolates strontium L-aspartate salt was formed in the trihydrate form.

To summarize, the present inventors have found that different strontium salts require different synthesis pathways, and for some strontium salts they have identified optimized synthesis and manufacturing procedures. Of particular relevance for the present invention, it has been found that synthesis of strontium salts of the di-carboxylic amino acids aspartate and glutamate (in either D- or L-form) and strontium malonate is very difficult when following the conventional reaction pathways, and generally results in low yields and purity of the obtained crystalline salt. In order to facilitate large-scale manufacture of pure strontium salts of dicarboxylic amino acids to carry out e.g. pharmaceutical use, the present inventors have studied various synthesis pathways of these particular strontium salts. Thus, it has surprisingly been found that synthesis of well defined and pure strontium glutamate in hexahydrate form is most conveniently performed with the free acid form of glutamate and strontium hydroxide and requires elevated temperatures, such as temperatures above 80° C., or more preferred 100° C. or even 120° C. or most preferred more than 130° C. (see Examples 5-17). Furthermore, they have found that addition of small volumes of alcohol can accelerate the crystal-formation of dissolved aqueous organic strontium salts (see Example 3). Furthermore, in the present invention new crystalline forms of strontium salts of dicarboxylic acids are disclosed (see Example 5, 6 and 10).

The strontium salts prepared according to the invention may be used in medicinal products, such as creams, lotions, ointments, tablets, capsules, gels etc. As mentioned above strontium is believed to have an effect on cartilage and/or bone conditions and/or other conditions, thus the salt may be used for the preparation of a pharmaceutical composition for the treatment and/or prophylaxis of a cartilage and/or a bone condition and/or a dysregulation of cartilage and/or bone metabolism in a mammal, such as osteoporosis, healing of skeletal fracture, stabilization of orthopaedic implants, osteoarthritis, rheumatoid arthritis, Legg-Calve-Perthes disease, steroid induced osteoporosis, bone loss induced by other therapies such as chemotherapy or highly active antiretroviral therapy (HAART) or systemic lupus erythomatosus (SLE) The pharmaceutical composition may further comprise one or more physiologically acceptable excipients.

For the treatment and/or prophylaxis of a cartilage and/or bone disease and/or conditions resulting in a dysregulation of cartilage and/or bone metabolism in a mammal, the possibility of administering various amounts of strontium and, if relevant malonate, alpha-ketoglutarate or an amino acid like e.g. glutamic acid and/or aspartic acid, respectively, may be desired. The amount of strontium (and, if relevant e.g. malonate, alpha-ketoglutarate or an amino acid) in a pharmaceutical composition according to the invention may be adjusted by adding an additional amount of strontium in the form of a strontium-containing compound to the composition. The strontium-containing compounds may be selected from the salts mentioned above.

In the following is given a more detailed description of the preparation of individual salts according to the invention. All details with respect to strontium apply also for all the other alkaline earth metal salts or salts of alkali metals according to the invention.

Furthermore, the details and particulars described above for strontium salts apply mutatis mutandis to the individual strontium salts, whenever relevant, as well as details and particular described below for the individual strontium salts apply mutatis mutandis to the strontium salts in general, whenever relevant. Furthermore, the methods of the present invention apply with equal relevance to the manufacturing of other metallo-organic salts.

EXAMPLES

Example 1—For Comparison

Use of a Known Method for Preparation of Crystalline Salts of Strontium by Precipitation from Dissolved Strontium Chloride and Dissolved Sodium Salts of the Appropriate Carboxylic Anions In a glass-beaker of 100 mL volume, 5 g of the sodium salt of the carboxylic acid was dissolved in a small volume of water that was slightly heated at temperatures not greater than 30-50° C. The final volume was 25-50 mL. In another beaker 10 g of $SrCl_2$ ($SrCl_2$ hexahydrate, Sigma-Aldrich 43, 966-5) was dissolved in 100 mL of water. This latter solution was slowly decanted into the first solution of the dissolved sodium salt. The transfer continued until an initial cloudiness was observed, which resulted in a total volume of 50-100 mL. The solution was incubated at room temperature (22-24° C.) for several days until significant amounts of crystallized precipitate of the organic strontium salt appeared.

The reaction that proceeds is exemplified by the reaction between strontium ions and sodium fumarate (reaction schemes (a) and (b)):

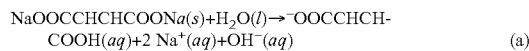

(a)

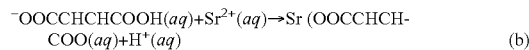

(b)

After the precipitation, the solution was filtered on a Büchner funnel using a suction flask and the crystals were flushed in small volumes of ethanol. Crystals of some of the salts were very soluble, so in order to improve the yield of crystals, the solution was allowed to rest longer, such as at least 30-60 min. Repeated crystallization resulted in yields of approx. 50%. Strontium salts of L-aspartate and of lactate were very soluble, with solubility exceeding 25 g/l in water at room temperature.

The lactate and L-glutamate salts of strontium were precipitated from solutions with an excess of strontium chloride and large crystals of the lactate salt were achieved by slow evaporation of the solvent.

Example 2—For Comparison

General Method for Preparation of Crystalline Salts by Neutralization of Carboxylic Acids with Strontium Hydroxide A small amount of the appropriate organic acid proper (0.75-3 g, see table below) was dissolved in water by heating to temperatures between 30° C.-50° C. Then, strontium hydroxide (Sigma Aldrich, Sr $(OH)_2*8H_2O$, MW 265.71, CAS no. 1311-10-0, approx. 10 g/L) was slowly added. Then, a magnetic stirring rod was added and the stirring and gentle heating (i.e. 30-50° C.) of the suspension was started. After some time, the solution clarifies and all the solid material dissolves. The heating is maintained, and after three hours of incubation, the solution is filtered while hot on a Büchner funnel. Very small amounts of impurities were left in the filter.

The filtrate was subsequently allowed to cool at room temperature overnight, which resulted in growth of fine-powdered crystals of the desired strontium salt. Further purifications of the salts can be performed by repeated re-crystallizations (Table 2).

TABLE 2

Amounts of start reagent used for organic strontium salt synthesis and recoveries in the synthesis of eight specific organic strontium salts following the general reaction pathway with free-acid forms of the anion, and strontium hydroxide

| Strontium salt of (free acid used): | $Sr(OH)_2*8H_2O$ | Free acid | Amount obtained | Estimated Yield * | Melting Temp. | Solubility | Crystal structure |
| --- | --- | --- | --- | --- | --- | --- | --- |
| Fumarate[1] | 2.044 g | 1.140 g | 0.999 g | 21% | >380° C. | Yes | No |
| α-ketoglutarate[2] | 2.017 g | 1.441 g | 0.828 g | 16% | >380° C. | Yes | No |
| Succinate | 2.098 g | 1.177 g | 0.958 g | 20% | 230° C. | Yes | Yes |
| L-ascorbate[3] | 2.094 g | 1.805 g | 2.005 g | 32% | >380° C. | Yes | No |
| L-glutamate | 2.017 g | 1.453 g | 0.175 g | 4% | >380° C. | Yes | Yes |
| Citrate | 2.057 g | 1.918 g | 1.123 g | 15% | >380° C. | Yes | Yes |

TABLE 2-continued

Amounts of start reagent used for organic strontium salt synthesis and recoveries in the synthesis of eight specific organic strontium salts following the general reaction pathway with free-acid forms of the anion, and strontium hydroxide

| Strontium salt of (free acid used): | $Sr(OH)_2 *8H_2O$ | Free acid | Amount obtained | Estimated Yield * | Melting Temp. | Solubility | Crystal structure |
|---|---|---|---|---|---|---|---|
| L-Aspartate | 2.190 g | 1.316 g | 0.167 g | 3% | >380° C. | No | No |
| Tartrate | 2.070 g | 1.502 g | 2.005 g | 36% | >380° C. | Yes | Yes |

Notes
* Recovery calculated in % of the strontium content in $Sr(OH)_2 *8H_2O$ and a stoichiometry that corresponds to the minimum content of the corresponding acid, e.g. a 1:1 ratio in the tartrate. The strontium salts of Table 2 (above) was characterised by powder x-ray crystallography and the corresponding diffractograms (not shown) showed that the product were relativelyimpure and of poor quality (i.e. heterogeneous crystal forms). Accordingly, the maximum yield of the room-temperature synthesis was evaluated to be 30%, which was calculated from the magnitude of characteristic peaksin the x-ray diffractograms. Weights were thus multiplied by a factor 0.3, as to obtain the estimated recovery and molecular weights of the strontium salts were used with the relevant amounts of bound crystal water. Although imprecise, the method reveals that the white powders of Table 2 did not contain high yields of the desired product. The remaining fraction ofthe product mainly consisted of unreacted reagents (i.e. strontiumhydroxide) and strontium carbonate. If the strontium salts of Table 2 contained six water molecules in the crystal structure than the yield would be reduced even further by some 10-50%, as compared to the values presented. These estimates and difficulties in determination results from formation substantial amounts of strontium carbonate when the salts were separated by re-crystallisation.
1) Fumaric acid is insoluble in water, and ethanol is added to the suspension until complete solubilization is achieved. The synthesis is continued with this material.
2) The strontium-AKG salt has a slight brownish appearance.
3) In addition to the indicated amounts of strontium hydroxides and L-ascorbate an additional 4.087 g $SrCl_2*6H_2O$ dissolved in water is added to the reaction mixture.

In conclusion, the methods known for the preparation of strontium salts result in a relatively poor yield (at the most less than 40%). Furthermore, the data in this example demonstrates that strontium carbonate formation, heterogeneous crystal formation and presence of unreacted starting products in the reactant product is a general phenomenon when synthesizing strontium salts by methods disclosed in the prior art literature. In the following Examples is given guidance for how to prepare strontium salts with a higher yield. The examples given below are intended for illustrative purposes and are not constructed to limit the invention in any way. Furthermore, a person skilled in the art can find guidance for preparation of other alkaline earth metal salts or organo-metallic compounds of interest according to the present invention.

Example 3

Improvement of Known Synthesis Methods for Making Metallo-Organic Salts by Using Ethanol Precipitation As an improvement of the method described in Examples 1 and 2, the present inventors have found that in order to accelerate the crystallization, addition of small volumes of an alcohol such as, e.g., methanol or ethanol, such as from 5-10 vol/vol % to 50-60% vol/vol induces a significant acceleration of the precipitation of the desired strontium salt. Addition of ethanol is of special importance in the synthesis of strontium salts with solubility exceeding 2 g/l at room temperature (22-24° C.), and will thus provide a substantial benefit for the synthesis of strontium salts of L-aspartate, L-glutamate and lactate. In order to reach the required product within a short period, it was essential to observe an initial crystallization or an initial dimness in the solution right from the first stage.

In the following example is given guidance for determination of the solubility of strontium salts in order to obtain information on whether alcohol precipitation advantageously can be applied to speed up and increase the crystallization of the specific strontium salt during its preparation according to the present invention.

Example 4

Determinations of Solubility of Organic Strontium Salts

Synthesis of Strontium Salts

The great majority of strontium salts could be obtained by reacting the sodium salt of the organic acid with strontium chloride following the general synthesis method described in Example 1. However, strontium citrate, strontium tartrate, strontium succinate and strontium ☐-ketoglutarate for the solubility investigations was obtained by synthesis from the free acid forms of the carboxylic acid and strontium hydroxide as described in Example 2. The solubility of the organic carboxylic acid strontium salts, were measured in purified water. The solubility of these salts was also measured as a function of temperature. This was performed by incubating the saturated solutions of the salts in temperature controlled incubators. Furthermore, the solubility of the salts was studied in pure distilled water as well as a 0.05 M ammonium carbonate buffered solutions, with a physiological pH of 7.5.

The buffered solutions were immersed into a water-bath temperature controlled at either room temperature (22-24° C.), at 30° C. or at 40° C. The test tubes were stirred and the solutions were subsequently incubated in an incubator with constant temperature for 24 hours. In order to eliminate the potential influence of any remaining strontium chloride on the determination of solubility, all the precipitate was collected at the bottom of the test tubes and the solutions above the precipitate were carefully removed and substituted by fresh solutions. After substitution of the solutions, the test tubes were stirred again and allowed to rest for another 24 hours. From these solutions, the dissolved proportions of the strontium salt were collected in volumes of 1 mL at the specified temperature. The solutions were diluted to 50 mL before analysis by Flame Atomic Absorption Spectrometry (F-AAS). Before subsequent series of sampling, the solutions were equilibrated at the next temperature for 24 hours.

Analysis of Strontium by Flame Atomic Absorption Spectrometry F-AAS

Two methods were used for quantification of strontium in solutions: Flame Atomic Absorption Spectrometry (F-AAS), and the more sensitive inductively-coupled-plasma-mass spectrometry (ICP-MS). For most investigations, the F-A-AS method had sufficient sensitivity.

Some of the very soluble strontium salts were further diluted before analysis by F-AAS. The measurements were performed by using a Perkin-Elmer 2100 equipped with a hydrogen lamp for correction of the background signal. Strontium was measured at a slit with of 0.2 nm, the wavelength was 460.8 nm operated at an energy of 58 and a current of 8 mA.

Temperature and pH Influence on Organic Strontium Salt Solubility

For the majority of the organic strontium salts listed in Table 3, temperature changes in the interval from 20-40° C. had only little influence on solubility (Table 3). However, for strontium L-glutamate a significant influence of temperature on solubility was observed in the range between 20° C. and 40° C. The solubility of this salt increased more than threefold in the investigated interval in contrast to most other salts. It is noted, that the solubility under physiological conditions (37° C.), is of relevance for the pharmaceutical use of the substances, and thus the surprising increase in strontium glutamate solubility at higher temperature may have great potential therapeutic implications.

The solubility of the strontium salts in an ammonium carbonate buffered solution of pH 7.5 was generally higher than the solubility determined in pure water (Table 3). However, there were some notable exceptions, such as strontium maleate, which had decreased solubility in the buffered solution. Accordingly, it was found most relevant to compare the solubility of the strontium salts by comparing the values obtained in water, as shown in Table 3.

Relative Solubility

The water-solubilities of the organic strontium salts at room temperature and at 40° C., are listed in table 3. The strontium salts of L-aspartate and of lactate had solubilities exceeding 50 g/l hampering exact determination of solubility with the employed experimental procedures.

The results are in agreement with the observations during the synthesis experiments where the citrate, the fumarate and the tartrate precipitated instantly when synthesized by the production procedures described in Examples 1 and 2. This is indicative of a poor solubility of these strontium salts, as apparent by the lower solubility of these salts compared to the other organic strontium salts at both 22° C. and 40° C.

The glutamate salt showed a higher solubility than the other salts, especially at a temperature of 40° C. During the synthesis of this salt, the present inventors found a significant improvement in the yield of the salt by adding alcohol to the solution, as described in Example 3. The addition of alcohol promoted the initiation of crystal growth. The other studied strontium salts only precipitated after evaporation of the solvent for a few days at room temperature. Addition of alcohol was not required to initiate crystal formation and precipitation, but it significantly promoted the precipitation and thus improved upon the synthesis method and the yields of the desired salts.

TABLE 3

Relative solubility in water buffered solutions at pH 7.5 at 40° C. and room temperature (22-24° C.) of the investigated Strontium-salts, as determined by F-AAS.

| STRONTIUM SALT | SOLUBILITY AT ROOM TEMPERATURE (22-24° C.) (mg/L) | | SOLUBILITY AT 40° C. (mg/L) | |
|---|---|---|---|---|
| Anion | In water | pH 7.5 | In water | pH 7.5 |
| Malonate** | 1474 | 2816 | 1441 | 2127 |
| L-glutamate** | 2111 | 3022 | 7093 | 7195 |
| L-aspartate** | >25000 | >25000 | >25000 | >25000 |
| Pyruvate* | 2204 | 1946 | 1929 | 1829 |
| □-ketoglute rate** | 1316 | 2252 | 3534 | 3809 |
| Fumarate** | 571 | 1215 | 444 | 977 |
| Maleate** | 3002 | 1680 | 2527 | 1457 |
| Tartrate** | 883 | 1831 | 1028 | 1400 |
| Ranelate**** | 760 | 890 | 1450 | 1970 |
| Succinate** | 1137 | 926 | 1116 | 2233 |
| Citrate*** | 107 | 388 | 147 | 430 |

*Mono-carboxylic acid
**Di-carboxylic acid - the glutamate salt is the hexahydrate salt
***Tri-carboxylic acid
****Tetra-carboxylic acid Example 5

Preparation of a Novel Salt, Strontium (L-) Diglutamate Pentahydrate, by Synthesis at 100° C. According to the Invention Initially, a suspension of glutamic acid (white colored) is prepared by adding 100 mL of millipore water to 14.703 g (0.1 moles) of solid L-glutamic acid (Sigma Aldrich, $C_5H_9NO_4$, MW 187.14 g/mole, CAS no. 142-47-2, lot. no. 426560/1, filling code 43003336) in a 250 mL beaker. To this suspension was added 26.66 g (0.1 moles) of solid $SrCl_2$ ($SrCl_2$ hexahydrate, Sigma-Aldrich 43, 966-5, MW 266.6). Then, a magnetic stirring rod was added and the stirring and heating was started, and maintained until the suspension reached the boiling point. The final suspension is also opaque white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, ethanol was added, which resulted in growth of fine-powdered crystals of strontium L-diglutamate pentahydrate. Precipitation of the final product progressed in the filtrate within an hour. The product was filtered and dried at 110° C. in an oven for ½ hour followed by drying 12 hours in a dessicator over silica orange. Before analysis by x-ray crystallography and by FAAS, the salts were ground by a mortar to fine powder.

The X-ray crystallographic analysis (see FIG. 1) revealed that the synthesized strontium glutamate salt was distinct from the previously described strontium L-glutamate hexahydrate salt (H. Schmidbaur, I. Bach, L. Wilkinson & G. Müller (1989), Chem. Ber. 122; 1433-1438). The strontium glutamate hexahydrate described previously in the literature by Schmidbaur et al. was reported to have very low solubility (0.023 g/l), wheras the strontium glutamate salt prepared by the method disclosed in the present example had a solubility above 2 g/l. This later parameter is very important for potential medical use of the strontium salt as described in the present invention. The salt was identified as a new glutamate salt of strontium: strontium L-diglutamate, containing two mono-hydrated glutamic acid moieties complexed to one strontium ion as a pentahydrate salt. The coordinates for the salt were identified as follows:

Strontium (L-) diglutamate pentahydrate was formed in uniform crystals belonging to the Monoclinic $P2_1$ space group with a unit size of a=8.7097 Å, b=7.2450 Å and c=14.5854 Å, Volume: 904.891 (0.158) Å$^3$. For detailed description of the X-ray crystallography procedure please see Example 18.

Figure 3:
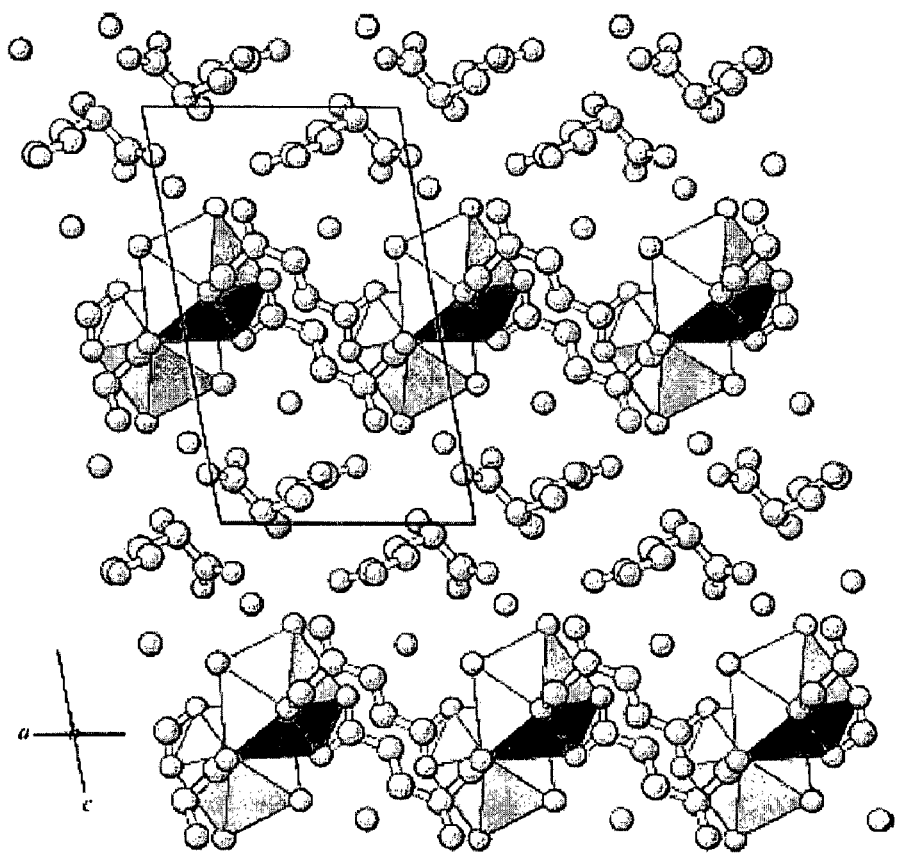
FIG. 3 shows the crystal packing of strontium (L-) diglutamate pentahydrate viewed along the b axis. The strontium nine coordination is shown as gray shaded polyhedra. H atoms have been omitted for clarity.
Figure 4:
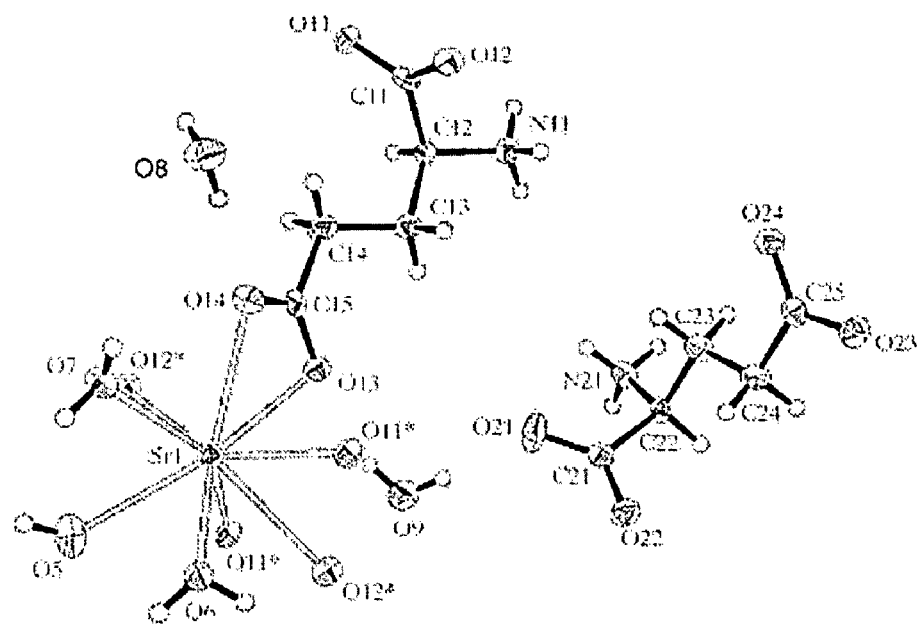
FIG. 4 illustrates the asymmetric unit of Strontium (L-) diglutamate pentahydrate crystals, showing 75% probability displacement ellipsoids and the atomic numbering. H atoms are represented by circles of arbitrary size.

The Strontium (L-) diglutamate pentahydrate crystal-composition is depicted in FIGS. 3 and 4.

TABLE 4

Figure 5:
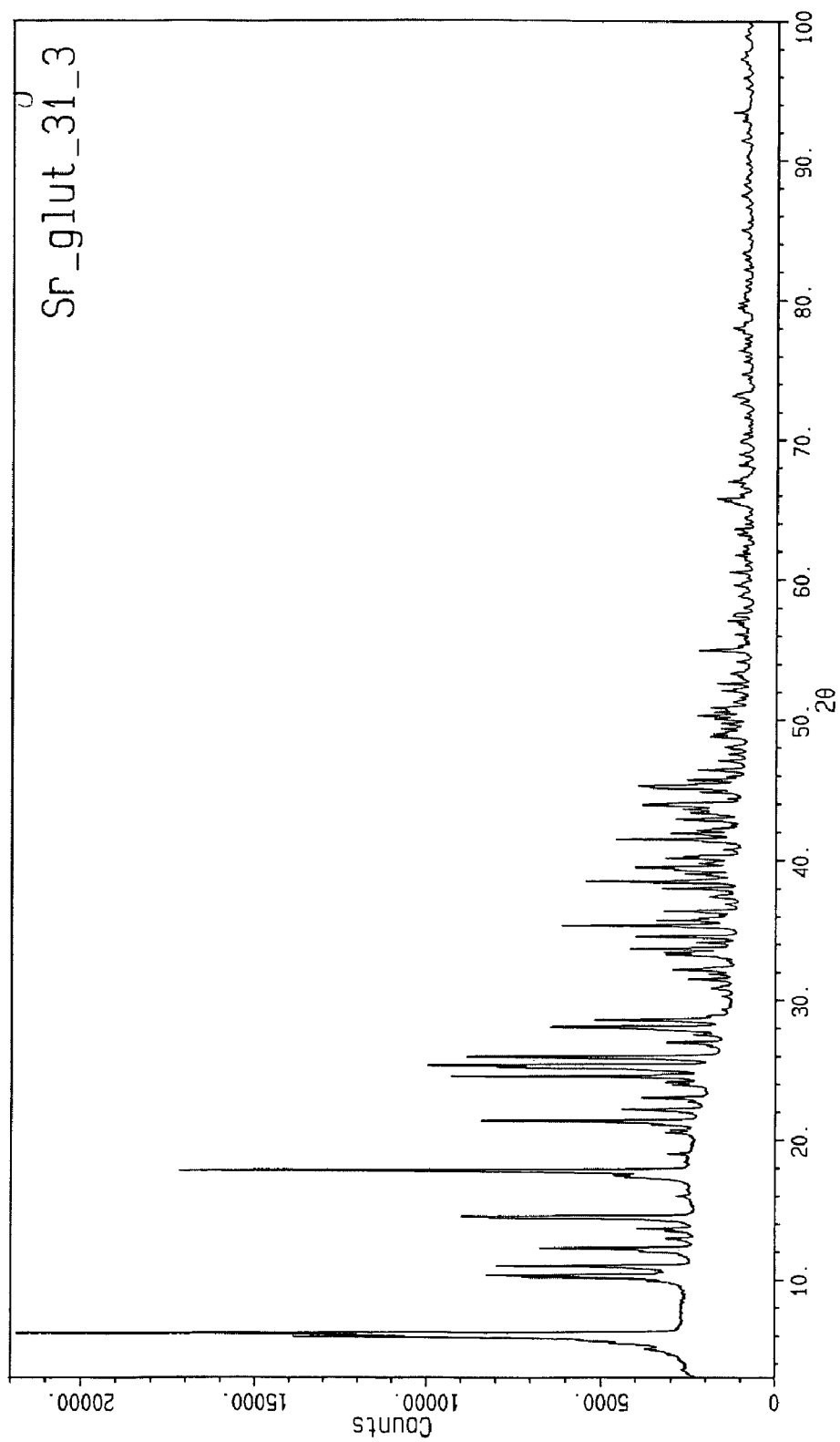
FIG. 5 shows a X-ray powder diffractogram of crystals of strontium glutamate hexahydrate prepared by the method as described in Example 8.
Figure 6:
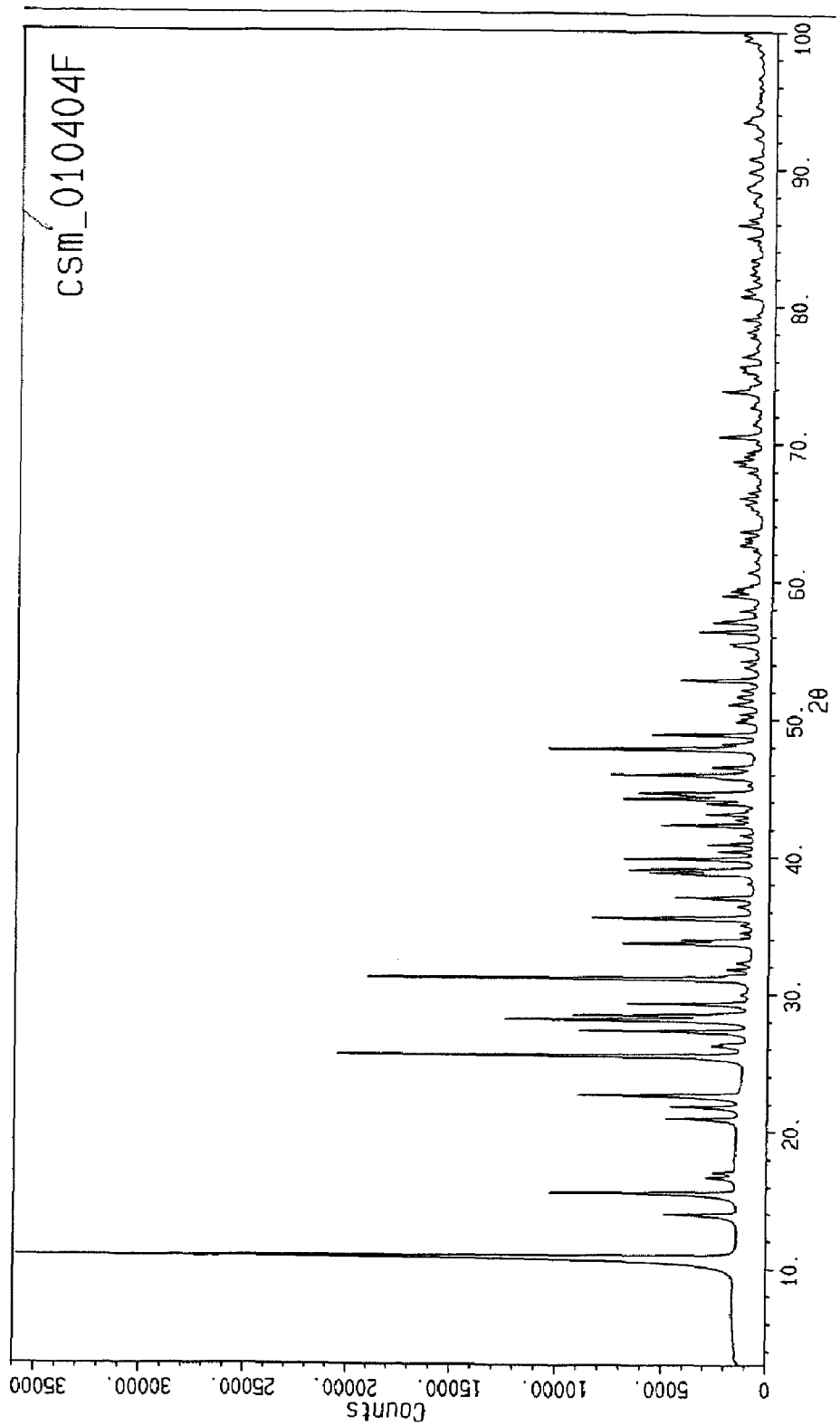
FIG. 6 shows a X-ray powder diffractogram of crystals of strontium malonate prepared by the method as described in Example 9 and analyzed as described in Example 18.

Key interatomic distances (Å) for Strontium (L-) diglutamate pentahydrate crystals. Atomic numbering used are as depicted in FIG. 5. All H atom parameters were initially refined freely. In the final cycles of Rietweld refinement, H atoms of $CH_2$ and CH groups were placed in calculated positions with C-H distances of 0.97 Å and 0.98 Å respectively and refined as riding atoms. For the water molecules in the crystal structure, the O-H distances were restrained to 0.84 Å and the N-H distances were restained to 0.89 Å. The displacement parameters were set to 1.2 (CH and NH) or 1.5 (OH) times $U_{eq}$ of the corresponding C, N or O atoms.

| | | | |
|---|---|---|---|
| SR1-O11$^{(xi)}$ | 2.603 (2) | Sr1-O11$^{(xii)}$ | 2.636 (2) |
| Sr1-O5 | 2.605 (2) | Sr1-O12$^{(xiii)}$ | 2.639 (2) |
| Sr1-O14 | 2.6130 (13) | Sr1-O13 | 2.6478 (12) |
| Sr1-O6 | 2.619 (2) | Sr1-O12$^{(xii)}$ | 2.816 (2) |
| Sr1-O7 | 2.6326 (16) | | |

Symmetry codes:

$^{(xi)}-x+1, y-\frac{1}{2}, -z+1;$ $^{(xii)}x+1, y, z;$ $^{(xiii)}-x+1, y+\frac{1}{2}, -z+1.$

TABLE 5

Hydrogen bond geometry (Å,°) of Strontium (L-) diglutamate pentahydrate. Atomic numbering used are as depicted in FIG. 5.

| D-H...A | D-H | H...A | D...A | D-H...A |
|---|---|---|---|---|
| N11-H12...O9$^{(x)}$ | 0.89 (2) | 1.88 (2) | 2.769 (3) | 171 (3) |
| N11-H13...O7$^{(xi)}$ | 0.87 (2) | 2.19 (2) | 3.004 (3) | 155 (2) |
| N11-H14...O23$^{(iii)}$ | 0.88 (2) | 1.87 (2) | 2.715 (3) | 161 (2) |
| N21-H22...O24$^{(xiv)}$ | 0.92 (2) | 1.93 (2) | 2.840 (3) | 173 (3) |
| N21-H23...O23$^{(iii)}$ | 0.88 (2) | 1.96 (2) | 2.805 (3) | 162 (2) |
| N21-H24...O22$^{(xv)}$ | 0.89 (2) | 1.88 (2) | 2.760 (3) | 168 (2) |
| O5-H1...O13$^{(xvi)}$ | 0.80 (2) | 1.95 (2) | 2.743 (3) | 177 (4) |
| O5-H2...O21$^{(xvi)}$ | 0.83 (2) | 1.95 (2) | 2.736 (3) | 158 (3) |
| O6-H3...O13$^{(xvii)}$ | 0.82 (2) | 1.89 (2) | 2.698 (3) | 173 (4) |
| O6-H4...O8$^{(xii)}$ | 0.83 (2) | 1.93 (2) | 2.738 (3) | 167 (2) |
| O7-H5...O22$^{(xvi)}$ | 0.81 (2) | 1.96 (2) | 2.763 (2) | 170 (3) |
| O7-H6...O24$^{(xiii)}$ | 0.80 (2) | 2.08 (2) | 2.852 (2) | 163 (3) |
| O8-H7...O14 | 0.81 (2) | 1.91 (2) | 2.722 (2) | 178 (4) |
| O8-H8...O5$^{(x)}$ | 0.83 (2) | 2.11 (2) | 2.866 (2) | 150 (3) |

TABLE 5-continued

Hydrogen bond geometry (Å,°) of Strontium (L-) diglutamate pentahydrate. Atomic numbering used are as depicted in FIG. 5.

| D-H...A | D-H | H...A | D...A | D-H...A |
|---|---|---|---|---|
| O9-H9...O21 | 0.83 (2) | 1.92 (2) | 2.745 (3) | 176 (3) |
| O9-H10...O6$^{(xvi)}$ | 0.81 (2) | 1.99 (2) | 2.765 (3) | 161 (3) |

Symmetry codes:

$^{(iii)}x, y+1, z;$ $^{(x)}x-1, y, z;$ $^{(xi)}-x+1, y-\frac{1}{2}, -z+1;$ $^{(xii)}x+1, y, z;$ $^{(xiii)}-x+1, y+\frac{1}{2}, -z+1;$ $^{(xiv)}-x+1, y+\frac{1}{2}, -z+2;$ $^{(xv)}-x+2, y+\frac{1}{2}, -z+2;$ $^{(xvi)}-x+2, y+\frac{1}{2}, -z+1;$ $^{(xii)}-x+2, y-\frac{1}{2}, -z+1.$

TABLE 6

Torsion angles (°) of Strontium (L-) diglutamate pentahydrate. Atomic numbering used are as depicted in FIG. 5.

| | (I) | (II:1) | (II:2) |
|---|---|---|---|
| O1-C1-C2-C3 | −107.3 (3) | −109.8 (2) | 91.3 (3) |
| C1-C2-C3-C4 | 54.5 (3) | 55.1 (3) | 70.7 (3) |
| C2-C3-C4-C5 | −178.5 (2) | 177.4 (2) | −179.6 (2) |
| C3-C4-C5-O3 | −56.3 (4) | −43.5 (4) | −170.6 (2) |
| O1-C1-C2-N1 | 17.5 (3) | 128.3 (2) | −28.3 (3) |
| N1-C2-C3-C4 | −73.0 (3) | 176.8 (2) | −169.4 (2) |

Further improvements of the synthesis of strontium (L-) diglutamate pentahydrate may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 6

Preparation of Strontium Aspartate Trihydrate by Synthesis at 100° C. According to the Invention Initially, a suspension of aspartic acid (white colored) is prepared by adding 100 mL of millipore water to 13.311 g (0.1 moles) of solid L-aspartic acid (Fluka, $C_5H_9NO_4$, MW133.11 g/mole, CAS no. 56-84-8, lot. no. 432866/1, filling code 52603495) in a 250 mL beaker. To this suspension was added 26.571 g (0.1 moles) of solid strontium hydroxide (Sigma Aldrich, Sr $(OH)_2*8H_2O$, MW 265.71, CAS no. 1311-10-0). Then, a magnetic stirring rod was added and the stirring and heating was started to the point of boiling of the suspension. The final suspension is also white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium aspartate trihydrate. Precipitation of the final product progressed in the filtrate within an hour. The product was filtered and dried at 110° C. in an oven for ½ hour followed by drying 12 hours in a dessicator over silica orange. Before analysis by x-ray crystallography and by FAAS, the salts were ground by a mortar to fine powder.

The total yield of strontium aspartate trihydrate was approximately 98% before recrystallisation, and the majority of impurities consisted of reminisces of the reagents and of strontium carbonate. This yield is significantly higher than the yield obtained by synthesis under conventional conditions where only 3% was obtained (see Example 2). Thus the high temperature synthesis method as disclosed herein provides a significant gain in yield and a reduction in synthesis time, while resulting in a strontium aspartate salt of higher purity. The product was unambiguously identified as strontium aspartate trihydrate by x-ray crystallography and comparing the data to results of the Cambridge Crystallographic Database and information from H. Schmidbaur, P. Mikulcik & G. Müller (1990), Chem. Ber. 123; 1599-1602. For detailed description of the X-ray crystallography procedure see Example 18.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 7

Preparation of Strontium Malonate Anhydrate by Synthesis at 100° C. According to the Invention Initially, a suspension of malonic acid (white colored) is prepared by adding 100 mL of millipore water to 10.406 g (0.1 moles) of solid malonic acid (Fluka, , MW 104.06 g/mole, CAS no. 141-82-2, lot. no. 449503/1, filling code 44903076) in a 250 mL beaker. To this suspension was added 26.571 g (0.1 moles) of solid strontium hydroxide (Sigma Aldrich, Sr $(OH)_2*8H_2O$, MW 265.71, CAS no. 1311-10-0). Then, a magnetic stirring rod was added and the stirring and heating was started to the point of boiling of the suspension. The final suspension is also white colored and the stirring was sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium malonate. Precipitation of the final product progressed rapidly during filtration and the majority of the product was found in the filter (unheated). Only in rare instants, the precipitation progressed in the filtrate. The product was filtered and dried at 110° C. in an oven for ½ hour followed by drying 12 hours in a dessicator over silica orange. Before analysis by x-ray crystallography and by FAAS, the salts were ground by a mortar to fine powder.

The total yield of strontium malonate was approximately 98% before recrystallisation, and the majority of impurities consisted of reminisces of the reagents and of strontium carbonate. The product was unambiguously identified as strontium malonate (anhydrous) by x-ray crystallography and comparing the data to results of the Cambridge Crystallographic Database (please refer to description in Example 18).

In a further improvement of the synthesis, anhydrous strontium malonate was produced in 10 kg scale in a method according to the present invention indicative of the applicability of the method for larger scale synthesis. 15.80 kg Sr $(OH)_2*8H_2O$ was dissolved in 63.21 purified water and heated to 95-100° C. 5.63 kg malonic acid was dissolved in 4.11 purified water, filtered where after an additional 1.41 of water was added and the solution heated to 95-100° C. The two solutions were mixed in a closed reaction vessel under an inert nitrogen atmosphere and stirred under reflux for 20 min. Subsequently the heating was stopped and the solution was allowed to cool to 40-50° C. over 2-4 hours while strontium malonate was allowed to precipitate. The precipitate was filtered and the salt washed with an additional 13.21 of water, followed by drying to complete dryness at vacuum in a temperature of 70° C. 9.4 kg anhydrous highly pure strontium malonate was obtained as a uniform microcrystalline white powder, corresponding to a yield of 94%. The product was unambiguously identified as strontium malonate (anhydrous) by x-ray crystallography and comparing the data to results of the Cambridge Crystallographic Database. For detailed description of the X-ray crystallography procedure please see Example 18.

Example 8

Methods of Manufacture of Strontium Salts of Dicarboxylic Acids Using Temperatures Above 100° C. According to the Invention According to methods developed previously and described in details in Examples 1 and 2, synthesis of strontium salts of dicarboxylic organic acids, and especially strontium salts of amino acids can be difficult to produce in larger scale (i.e. >1 kg) due to low yields and difficulties in separating the desired reaction products from contaminants. Strontium salts of carbonate are of special concern, as they will form as impurities when the reaction is occurring in atmospheric air containing normal levels of carbon dioxide. In Examples 4-7 the present inventors have shown that the total yield of the product when strontium salts of dicarboxylic acids are manufactured from the free acid form of the anion and strontium hydroxide, depends on temperature and on time of synthesis. In order for the reaction to reach completion, the mixture of the appropriate amino acid and strontium hydroxide needs boiling in water, allowing ample time for strontium in the reaction mixture to react with carbon dioxide in the air, if no other means or procedures are employed to control the unwanted formation of strontium carbonate. In this example, the present inventors disclose methods of improving the synthesis further by providing optimized reaction conditions, where temperature is increased above 100° C. in a closed container, and where reaction times are significantly reduced, and where inert atmospheres of carbon-dioxide free gases easily can be introduced.

The present example provides representative data from the optimization of conditions for synthesis of strontium L-glutamate hexahydrate in an autoclave system. In contrast to the conditions employed in Example 5, strontium hydroxide is used as starting material, which results in the formation of strontium L-glutamate hexahydrate. Strontium L-glutamate is used as an example, but the optimizations described in the example is also applicable for the synthesis of other strontium salts, where the exact reaction conditions can be optimized as disclosed in this example. The reaction temperatures must be maintained below the melting point or below the temperature of decomposition of the organic anion moiety of the desired strontium salt.

Strontium L-glutamate was used as a model strontium compound in the optimization experiments. The purity of the product was monitored by comparing to crystallographic data and by measuring the content of strontium. Ideally, the content of strontium is 25.7% in strontium L-glutamate hexahydrate, which is the product formed in these experiments. It follows that other strontium salts may be prepared by similar methods with high yield and purity.

Experimental

Preparation of Solutions: a Suspension of Glutamic Acid (White Coloured) is prepared by adding 100 mL of millipore water to 14.703 g (0.1 moles) of solid L-glutamic acid (Sigma Aldrich, $C_5H_9NO_4$, MW 187.14 g/mole, CAS no. 142-47-2, lot. no. 426560/1, filling code 43003336) in a 250 mL beaker. To this suspension was added 22.257 g, 26.571 g or 31.885 g (0.08 moles, 0.1 moles or 0.12 moles) of solid strontium hydroxide (Sigma Aldrich, Sr $(OH)_2 \cdot 8H_2O$, MW 265.71, CAS no. 1311-10-0).

Optimisation Experiments

After preparation of the salts, the nine optimizations experiments were performed according to the settings of Table 7. In this table, the term 'base-acid ratio' indicates the molar ratio between strontium hydroxide and glutamic acid.

3. The bottle was placed in the autoclave and the temperature was set. While in the autoclave no additional stirring was carried out.
4. At t=100° C. the valve of the autoclave was closed and the timing was started.
5. During the autoclaving were monitored the actual temperature and the actual pressure.
6. After the time of autoclaving ended, the steam was let out, as soon as possible, with due respect to safety precautions.
7. At approx. 110° C. the autoclave was opened and the solution was recovered. Again, the bottle was shaken, as to obtain a high degree of mixing.
8. The solution was immediately filtered hot on a Büchner funnel after autoclaving, which left only traces of carbonate in the filter. The product precipitated from the solution during cooling to room temperature.
9. After precipitation, the product was filtered and dried in an oven for ½ an hour at 110° C. Then, it was dried in a dessicator over silica-gel orange. Finally, the product was ground to fine powder in a mortar.
10. The product was weighed after grinding and the total yield calculated.

Content of Strontium (% Sr):

A sample of 0.2 g was dissolved in 100 mL 0.1 M $HNO_3$ prepared in Millipore water. This solution was further diluted by a factor of 500 by a solution of 1% KCl, and the content of strontium was determined by FAAS. The measurements were performed by using a Perkin-Elmer 2100 equipped with a hydrogen lamp for correction of the background signal. Strontium was measured at a slit width of 0.2 nm, the wavelength was 460.8 nm operated at an energy of 58 and a current of 8 mA.

X-Ray Crystallography

A second check of purity was performed by powder x-ray crystallography using a Huber G670 diffractometer as

TABLE 7

Parameters and main results of the optimization procedure for synthesis of strontium L-glutamate. The pressure was monitored but not used in the optimization process. The strontium content (% Sr) was measured by FAAS but not used as quality parameter. The theoretical strontium content of strontium glutamate hexahydrate is 25.7%. The yield (%) was applied as the quality parameter.

| Experiment no. | Autoclave temperature (° C.) | Time of synthesis (min.) | Base-acid ratio | Total volume (ML) | Autoclave pressure (bar) | Yield % | % Sr (AAS) |
|---|---|---|---|---|---|---|---|
| 1 | 125 | 15 | 0.8 | 50 | 1.55 | 94 | 25 |
| 2 | 124 | 30 | 1 | 75 | 1 | 112 | 22 |
| 3 | 124 | 60 | 1.2 | 100 | 1.6 | 121 | 21 |
| 4 | 127 | 15 | 1 | 100 | 1.2 | 118 | 22 |
| 5 | 132 | 30 | 1.2 | 50 | 1.55 | 120 | 25 |
| 6 | 132 | 60 | 0.8 | 75 | 1.6 | 50 | 22 |
| 7 | 134 | 15 | 1.2 | 75 | 1.65 | 108 | 24 |
| 8 | 134 | 30 | 0.8 | 100 | 1.65 | 76 | 14 |
| 9 | 132 | 60 | 1 | 50 | 1.65 | 82 | 24 |

Procedure
1. The calculated amount of acid was weighed and transferred to a bluecap autoclave bottle and the Millipore water was added. The bottle was closed and shaken, in order to obtain a finely grained suspension.
2. The calculated amount of strontium hydroxide octahydrate was weighed and added to the acid solution of (1) and the bottle was vigorously vortexed until all coarse lumps of material were transformed into fine-grained powder.

described in more detail in Example 18. A characteristic diffractogram of the strontium glutamate is shown in FIG. 5.

Results and Discussion

From the results listed in Table 7 above, it is apparent that some of the synthesis conditions resulted in relatively low yield and in strontium glutamate of low purity as apparent from the molar % of strontium in the reaction product. The product of experiment no. 8 was produced in relatively low yield, and it did not contain the expected 25.7% of strontium.

However, in general, the outcome of the optimization experiments is close to the expected products. Incomplete reaction provides a product of too low content of strontium. Conditions employed in experiments 1 and 5 gave the strontium content in best agreement with the expected value.

By studying the influence of the individual parameters on the total yield (Table 4), it becomes clear that temperature, reaction time and base-acid ratios are important for the synthesis while total volume is less important. A yield higher than 100%, which is observed in experimental conditions 2, 3, 4, 5 and 7 (Table 7) originates from incomplete drying, but this effect is almost eliminated when the average values are considered.

The maximum yield was obtained by using a high temperature (133° C.), a short reaction time and a surplus of strontium hydroxide. Accordingly, temperature is more important than time but it compares in importance to the base-to-acid ratio. A $10^{th}$ experiment of control of optimization was performed, as to confirm the maximum yield of the optimization experiments, and the result of this experiment was in agreement with the findings reported in Table 7.

Further improvements of the synthesis include introduction of inert atmospheres to the synthesis environment, as well as degassing of all solutions by either nitrogen gas or by argon gas, as to reduce the formation of carbonate salts. Such salts may form readily in a normal air atmosphere and due to the very poor solubility of carbonate salts of most alkaline earth and alkali metals they will precipitate readily in the reaction mixture.

Example 9

Methods of Manufacture of Strontium Malonate Using Temperatures Above 100° C. According to the Invention In order to confirm the applicability of the disclosed high temperature synthesis method for strontium salts other than strontium L-glutamate, strontium malonate was prepared by the high temperature synthesis method. Basically the reaction conditions found for preparation of strontium L-glutamate (Example 8) was employed. A suspension of malonic acid (white coloured) is prepared by adding 100 mL of millipore water to 10.41 g (0.1 moles) of solid malonic acid (FLUKA 63290, MW 104.1, CAS 141-82-2) in a 250 mL beaker. To this suspension was added 22.257 g, 26.571 g or 31.885 (0.08 moles, 0.1 moles or 0.12 moles) of solid strontium hydroxide (Sigma Aldrich, $Sr(OH)_2 \cdot 8H_2O$, MW 265.71, CAS no. 1311-10-0). The reaction procedure described in Example 8 was followed, and the temperature was maintained below 130° C. to avoid decomposition of malonic acid, while the reaction time was maintained at 15 min.

Highest yield were obtained by the synthesis method using a molar ratio of $Sr(OH)_2$-to-acid of 1.2

Figure 7:
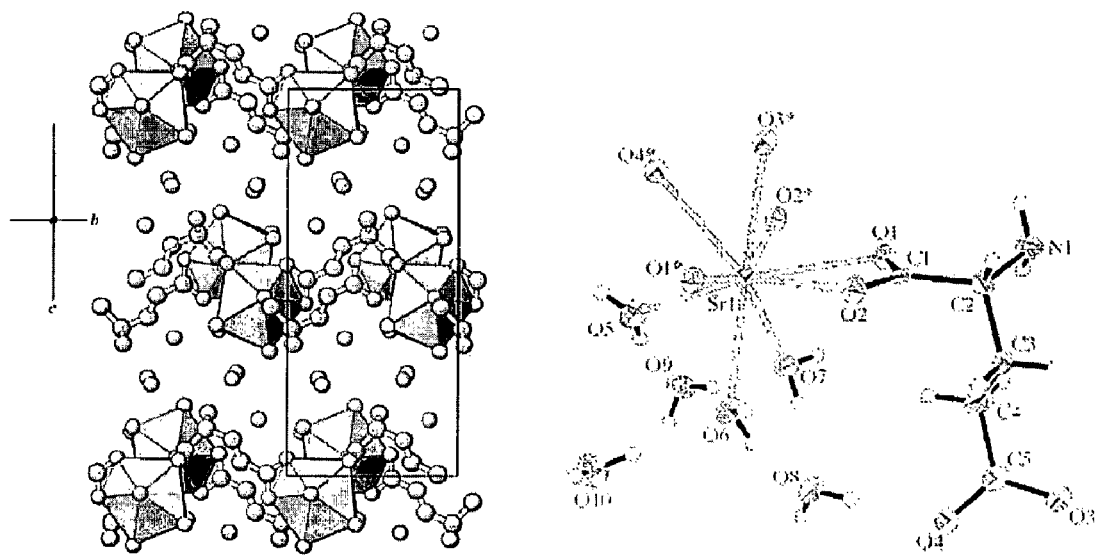
FIG. 7 illustrates the crystal packaging of strontium D-glutamate hexahydrate (left panel) and asymmetric unit of the crystals (right panel) showing 75% probability displacement ellipsoids and the atomic numbering. H atoms are represented by circles of arbitrary size. In the left panel the crystals are viewed down the α-axis, with the Sr nin-coordination shown as polyhedra.

An X-ray powder diffractogram of strontium malonate obtained by the high temperature synthesis method disclosed in the present example is shown in FIG. 7. For detailed description of the X-ray crystallography procedure please see Example 18.

The revealed X-ray diffractogram of the synthesized malonate salt of strontium is in agreement with the previously described anhydrous crystalline strontium malonate. It is apparent from the stable baseline, and well-defined spacing of diffraction peaks, that the crystal form of the malonate salt is homogeneous and pure. Thus crystalline pure and well defined strontium malonate could easily be obtained by the high temperature synthesis method.

Example 10

Preparation of a Novel Strontium Salt of D-Glutamic Acid by the High Temperature Synthesis Method An additional experiment was performed to validate the applicability of the high temperature synthesis method for the preparation of other racemic strontium salts. Strontium D-glutamate was chosen. This salt has not been prepared previously. It was synthesized by preparing a suspension of D-glutamic acid as follows: 14.713 g (0.1 moles) of solid D-glutamic acid (Sigma-Aldrich $HO_2CCH_2CH_2CH(NH_2)CO_2H$, MW 147.13, CAS no. 6893-26-1) was dissolved in 100 ml pure water in a 250 mL beaker. To this suspension was added 31.898 g (0.12 moles) of solid strontium hydroxide (Sigma Aldrich, $Sr(OH)_2 \cdot 8H_2O$, MW 265.71, CAS no. 1311-10-0). The reaction procedure described in example 8 was followed, and the temperature was maintained a 132° C. and the reaction time was maintained at 15 min. After completion of the reaction, the strontium D-glutamate salt was filtered, dried and subjected to X-ray diffraction analysis to reveal the structure as described in example 18.

Strontium D-glutamate hexahydrate in was formed in uniform crystals belonging to the orthorhombic $P2_12_12_1$ space group with a unit size of a=7.3244 Å, b=8.7417 Å and c=20.0952 Å, Volume: 1286.65 Å$^3$. The crystal form of strontium D-glutamate hexahydrate was similar to the previously described structure of strontium L-glutamate hexahydrate (H. Schmidbaur, I. Bach, L. Wilkinson & G. Müller (1989), Chem. Ber. 122; 1433-1438). FIG. 8 depicts the structure and unit cell geometry of the crystals The following coordinates were obtained (Table 8 and 9):

TABLE 8

Key interatomic distances for strontium D-glutamate with distances in Angstrom.

| | | | |
|---|---|---|---|
| Sr1-O1$^{(i)}$ | 2.623 (2) | Sr1-O3$^{(iii)}$ | 2.6639 (17) |
| Sr1-O5 | 2.625 (2) | Sr1-O2 | 2.6687 (18) |
| Sr1-O2$^{(ii)}$ | 2.635 (2) | Sr1-O6 | 2.693 (2) |
| Sr1-O7 | 2.637 (2) | Sr1-O1 | 2.7083 (19) |
| Sr1-O4$^{(iii)}$ | 2.6501 (17) | | |

Symmetry codes:

$^{(i)} x - \frac{1}{2}, -y + \frac{1}{2}, -z + 2;$ $^{(ii)} x + \frac{1}{2}, -y + \frac{1}{2}, -z + 2;$ $^{(iii)} x, y + 1, z.$

TABLE 9

Coordinates of strontium D-glutamate. Coordinates of hydrogen atoms are included in the table, and the atom numbering are as shown in FIG. 5.

| D-H...A | D-H | H...A | D...A | D-H...A |
|---|---|---|---|---|
| N1-H3...O4$^{(iv)}$ | 0.90 (2) | 2.40 (2) | 3.283 (3) | 169 (3) |
| O5-H8...O9$^{(v)}$ | 0.84 (2) | 1.95 (2) | 2.768 (3) | 163 (3) |
| O5-H9...O10$^{(vi)}$ | 0.81 (2) | 2.14 (2) | 2.939 (3) | 168 (3) |
| O6-H10...O8$^{(v)}$ | 0.80 (2) | 1.97 (2) | 2.740 (3) | 160 (4) |
| O6-H11...O3$^{(viii)}$ | 0.78 (2) | 2.01 (2) | 2.783 (3) | 170 (4) |
| O7-H12...O3$^{(iv)}$ | 0.81 (2) | 1.90 (2) | 2.713 (3) | 177 (3) |
| O7-H13...O8$^{(v)}$ | 0.83 (2) | 1.90 (2) | 2.719 (3) | 170 (3) |
| O8-H14...O10$^{(viii)}$ | 0.78 (2) | 1.94 (2) | 2.711 (3) | 171 (3) |

TABLE 9-continued

Coordinates of strontium D-glutamate. Coordinates of hydrogen atoms are included in the table, and the atom numbering are as shown in FIG. 5.

| D—H...A | D—H | H...A | D...A | D—H...A |
|---|---|---|---|---|
| O8—H15...O4$^{(v)}$ | 0.80 (2) | 1.91 (2) | 2.708 (3) | 176 (4) |
| O9—H16...O7$^{(v)}$ | 0.80 (2) | 2.00 (2) | 2.766 (3) | 163 (3) |
| O9—H17...N1$^{(ix)}$ | 0.81 (2) | 1.93 (2) | 2.735 (3) | 176 (3) |
| O10—H18...O9$^{(x)}$ | 0.81 (2) | 1.97 (2) | 2.775 (3) | 172 (4) |
| O10—H19...O6$^{(v)}$ | 0.80 (2) | 2.00 (2) | 2.796 (3) | 178 (4) |

Symmetry codes:

$^{(iv)} x + \frac{1}{2}, -y - \frac{1}{2}, -z + 2;$ $^{(v)} x, y, z;$ $^{(vi)} -x + 1, y + \frac{1}{2}, -z + \frac{3}{2}$ $^{(vii)} x - \frac{1}{2}, -y - \frac{1}{2}, -z + 2;$ $^{(viii)} -x + 1, y - \frac{1}{2}, -z + \frac{1}{2};$ $^{(ix)} -x + \frac{1}{2}, -y, z - \frac{1}{2};$ $^{(x)} x - 1, y, z.$ Example 11

Synthesis of Strontium Formate

Basically the reaction conditions found for preparation of strontium L-glutamate (example 8) was employed. A suspension of malonic acid (white coloured) is prepared by adding 100 mL of millipore water to 4.603 g (0.1 moles) of solid formic acid (FLUKA 33015, MW 104.1, CAS 64-18-6) in a 250 mL beaker. To this suspension was added 31.898 g (0.12 moles) of solid strontium hydroxide (Sigma Aldrich, Sr (OH)$_2$*8H$_2$O, MW 265.71, CAS no. 1311-10-0). The reaction procedure described in Example 8 was followed.

Example 12

Synthesis of Magnesium Malonate

Magnesium malonate in pure form was synthesized in high yield and purity using the reaction conditions found for preparation of strontium malonate (example 9). A suspension of sodium malonate (white colored) is prepared by adding 100 mL of millipore water to 16.605 g (0.1 moles) of solid sodium malonate dibasic monohydrate (SIGMA M1875-100 G, MW 166.05, CAS 26522-85-0) in a 250 mL beaker. To this suspension was added 24.410 g (0.12 moles) of solid magnesium chloride hexahydrate (FLUKA 63068, MgCl$_2$*6H$_2$O, MW 203.3, CAS 7791-18-6). The reaction procedure described in Example 8 was followed.

Example 13

Synthesis of Zinc L-Glutamate Dihydrate

Basically the reaction conditions found for preparation of strontium L-glutamate (Example 8) was employed. A suspension of sodium glutamate (white coloured) is prepared by adding 100 mL of millipore water to 18.714 g (0.1 moles) of solid L-glutamic acid monosodium salt monohydrate (ALDRICH G2834, MW 187.14, CAS 142-47-2) in a 250 mL beaker. To this suspension was added 13.628 g (0.1 moles) of solid zinc chloride (FLUKA, 96469, MW 136.28, CAS 7646-85-7). The reactants were placed in the sealed container in an autoclave, and temperature was increased to 132° C. for 15 min whereafter the reaction was stopped and after the reaction mixture reached a temperature of 92-98° C., it was filtered on a Büchner funnel, and the desired zinc L-glutamate salt readily precipitated from the filtrate. The yield was approximately 95% and purity higher than 96%.

Example 14

Synthesis of Zinc Malonate Dihydrate

Basically the reaction conditions found for preparation of zinc L-glutamate (Example 13) was employed. A suspension of sodium malonate (white coloured) is prepared by adding 100 mL of millipore water to 16.605 g (0.1 moles) of solid sodium malonate dibasic monohydrate (SIGMA M1875-100G, MW 166.05, CAS 26522-85-0) in a 250 mL beaker. To this suspension was added 13.628 g (0.1 moles) of solid zinc chloride (FLUKA, 96469, MW 136.3, CAS 7646-85-7). Subsequent manufacturing steps were as described in Example 13.

Example 15

Synthesis of Barium L-Glutamate

Basically the reaction conditions found for preparation of strontium L-glutamate (Example 8) was employed. A suspension of L-glutamic acid (white coloured) is prepared by adding 100 mL of millipore water to 14.713 g (0.1 moles) of solid L-glutamic acid (FLUKA 49449, MW 147.13, CAS 56-86-0) in a 250 mL beaker. To this suspension was added 37.86 g (0.12 moles) of solid barium hydroxide octa hydrate (FLUKA 11780, Ba (OH)$_2$*8H$_2$O, MW 315.5, CAS 12230-71-6). The reaction procedure described in Example 8 was followed.

Example 16

Synthesis of Calcium L-Glutamate

Basically the reaction conditions found for preparation of strontium L-glutamate (Example 8) was employed. A suspension of sodium glutamate (white coloured) is prepared by adding 100 mL of millipore water to 18.714 g (0.1 moles) of solid L-glutamic acid monosodium salt monohydrate (ALDRICH G2834, MW 187.14, CAS 142-47-2) in a 250 mL beaker. To this suspension was added 17.6424 g (0.12 moles) of solid calcium chloride dihydrate (FLUKA, 21097, MW 147.0, CAS 10035-04-8). The reaction procedure described in Example 8 was followed.

Example 17

Synthesis of Calcium Malonate

Basically the reaction conditions found for preparation of strontium malonate (example 9) was employed. A suspension of sodium malonate (white coloured) is prepared by adding 100 mL of millipore water to 16.605 g (0.1 moles) of solid sodium malonate dibasic monohydrate (SIGMA M1875-100 G, MW 166.05) in a 250 mL beaker. To this suspension was added 17.6424 g (0.12 moles) of solid calcium chloride dihydrate (FLUKA, 21097, MW 147.0, CAS 10035-04-8). The reaction procedure described in Example 8 was followed.

Example 18

Determination of Crystal Structure by X-Ray Diffraction

General

The inventors define a crystalline material as having a structure with a three-dimensional repetition, i.e. there is a smallest identical unit, the unit cell, which by translations in three dimensions will fit to any part of the crystal. The unit cell dimensions are typically between 3 and 25 Å for inorganic and organic materials. Such a three-dimensional array of unit cells will also contain sets of lattice planes connecting all corners of the unit cells. The distance between the lattice planes in such a set will be from zero up to the maximum dimension of the unit cell itself. The plane distances are thus in the same order of magnitude as the X-ray wavelength used for diffraction, 0.5-2.4 Å. When such a crystal is placed in an X-ray beam it will act as a grating to create a characteristic interference or diffraction pattern. The positions of the recorded diffracted radiation will be determined by the lattice plane distances, i.e. the size of the unit cell, while the recorded diffracted intensities are determined by the positions and symmetry of the atoms in the unit cell. For practical purposes it means that a unique crystal structure will produce a unique diffraction pattern that can be used for identification or to determine the crystal structure. There are two general methods commonly used for structure analysis: The single-crystal method and the powder diffraction method.

Single-Crystal Methods

This method is primarily used to determine the crystal structures of unknown materials. As the name implies just one crystal, typically less than 0.3 mm in size, is used. The crystal is mounted on a single-crystal diffractometer where it can be rotated in independent directions and a complete three-dimensional diffraction pattern can be collected in about ten hours. From the positions of the diffraction spots the unit cell dimensions may be calculated and from the intensity of the spots the atomic arrangement within the unit cell may be solved. The solved structure is unique within the accuracy, typically better than 0.01 Å in interatomic distances and the method is also sensitive to the absolute confirmation of the molecules in the structure. With modern diffractometers and software the method is successful to 99% with organic and metal organic compounds.

Powder Diffraction

A powder sample will ideally contain an infinite amount of micrometer sized crystals in random orientation. When radiated by X-ray each of the crystallites will diffract independently and add its contribution to the diffraction pattern. As a result a powder diffraction pattern will be a one-dimensional projection of the three-dimensional single-crystal pattern. The interpretation of a powder diffraction pattern is much less straightforward than a single-crystal pattern. Depending on unit cell size and symmetry a powder diffraction pattern show various degrees of reflection overlap. Nevertheless, the peak positions are still a function of the unit cell dimensions and the intensities a function of the unit cell contents. A powder diffraction pattern is more or less a fingerprint of the investigated structure, and using a powder diffraction data base and an effective search-match program the present inventors can with 10 minutes of data collection and a few minutes analysis safely identify known structures. Powder diffraction has become the workhorse for structural characterization of materials in general. Except for phase identification, the method is commonly used for structure solution, structure refinements and for studies of crystallinity, crystallite size and size distributions, stress/strain etc. Although the method is primarily intended for solid crystalline materials, information from amorphous and fibrous materials and thin films is also readily obtained.

| Powder diffraction equipment | |
|---|---|
| Diffractometer: | Huber G670 powder diffractometer operating in Guinier (transmission) geometry and equipped with a primary quartz focusing monochromator and an imaging plate detector with an integrated laser/photomultiplier read-out system |
| X-ray generator: | 40 kV and 30 mA. |
| Radiation: | CuKα1 1.54059 Å |
| Instrument calibration: | Intensity and 2θ-scale checked with a Si-standard (NBS) fitted through full pattern Rietveld refinements. Calibrated approximately once a week and after any adjustment of the diffractometer. |
| Sample holder: | Flat plate scotch tape, 10 by 10 mm active area in Scotch tape |
| Measurement: | Range: 2 to 100° in 2θ. Detector is read out in steps of 0.05° in 2θ. Exposure time is between 15 and 120 min depending on scattering power. |
| Measurement procedure: | The samples are ground by an agate mortar and pestle and put on the sample holder on the Scotch tape. The sample holder is mounted on the powder diffractometer mount and the rocking motor is started. In the data collection program the file name is given (typically the sample name) and any other comments or observations are entered. The measuring time is entered and the data collection started. The file name, measuring time and operator is written in the note book. After completed measurement the powder diffraction pattern is printed and signed by the operator. An attempt to identify the sample using the search-match program will usually be made. |

REFERENCES

Briggman B & Oskasson Å 1977, Acta Cryst. B33; 1900-1906

Schmidbaur H et al. Chem. Ber. (1989) 122: 1433-1438

Schmidbaur, H, P. Mikulcik & G. Müller (1990), Chem. Ber. 123; 1599-1602

The invention claimed is:

1. A method for the preparation of a strontium salt of an organic dicarboxylic acid, the method comprising reacting at least one of a hydroxide and/or a halogen inorganic salt of strontium with the organic dicarboxylic acid in an aqueous medium at a temperature of about 90° C. or more for a time period of at the most about 60 minutes in a reaction mixture, and wherein the molar ratio between the hydroxide and/or the halogen inorganic salt of strontium and the organic dicarboxylic acid is in the range from 1:1 to 1.2:1.

2. The method according to claim 1, wherein the molar ratio between the hydroxide and/or the halogen inorganic salt of strontium and the organic dicarboxylic acid is in the range from 1.05:1 to 1.2:1.

3. The method according to claim 1, wherein the molar ratio between the hydroxide and/or the halogen inorganic salt of strontium and the organic dicarboxylic acid is in the range from 1.1:1 to 1.2:1.

4. The method according to claim 1, wherein the molar ratio between the hydroxide and/or the halogen inorganic salt of strontium and the organic dicarboxylic acid is 1:1.

5. The method according to claim 1, wherein the organic dicarboxylic acid is selected from the group consisting of: fumaric acid, maleic acid, malonic acid, tartaric acid, oxalic acid, L- and D-glutamic acid, L- and D-aspartic acid, acetonedicarboxylic acid, adipic acid, alpha-ketoglutaric acid, azelaic acid, citraconic acid, cyclopentane-1,2-dicarboxylic acid, cystathionine, glutaconic acid, glutaric acid, itaconic acid, lanthionine, malic acid, mesaconic acid, pimelic acid, sebacic acid, suberic acid, succinic acid, and terephthalic acid.

6. The method according to claim 1, wherein the organic dicarboxylic acid is an amino carboxylic acid.

7. The method according to claim 1, wherein the strontium salt of the organic dicarboxylic acid is selected from the group consisting of strontium glutamate, strontium aspartate, strontium malonate, strontium D-glutamate, strontium L-glutamate, strontium (L-) diglutamate pentahydrate, strontium D-aspartate, strontium L-aspartate, strontium maleate, strontium fumarate and strontium succinate.

8. The method according to claim 7, wherein the strontium salt of the organic dicarboxylic acid is strontium malonate.

9. The method according to claim 1, wherein the at least one of a hydroxide and/or a halogen inorganic salt of strontium is the halogen inorganic salt of the strontium.

10. The method according to claim 9, wherein the halogen inorganic salt of strontium is a chloride salt.

11. The method according to claim 1, where the reaction is performed in a closed container at a temperature of 100° C. or more and a pressure of 1 bar or more.

12. The method according to claim 2 comprising reacting strontium hydroxide with the organic dicarboxylic acid at a temperature in a range of from about 120° C. to about 135° C. and at a pressure of from about 1 to about 1.7 bar for a time period of from about 15 minutes to about 60 minutes to obtain the strontium salt of the organic dicarboxylic acid.

13. The method according to claim 1 further comprising isolating the strontium salt of the organic dicarboxylic acid by precipitating the strontium salt from the reaction mixture by adding 5-60 vol/vol % alcohol to the reaction mixture.

14. The method according to claim 13, where the alcohol is ethanol.

15. The method according to claim 13, where the alcohol is methanol.

16. The method according to claim 1, wherein the temperature is about 100° C. or more.

17. The method according to claim 1, wherein the temperature is about 120° C. or more.

18. The method according to claim 1, wherein the temperature is about 125° C. or more.

19. The method according to claim 1, wherein the time period is at the most about 30 minutes.

20. The method according to claim 1, wherein the time period is at the most about 20 minutes.

21. The method according to claim 1, wherein the time period is about 15 minutes.

22. The method according to claim 6, wherein the amino carboxylic acid is a natural amino acid.

23. The method according to claim 6, wherein the amino carboxylic acid is a synthetic amino acid.

24. The method according to claim 13 wherein 5-40 vol/vol % alcohol is added to the reaction mixture.

25. The method according to claim 13 wherein 10-25 vol/vol % alcohol is added to the reaction mixture.

26. The method according to claim 1, wherein said reacting is conducted under an inert gas or steam atmosphere.

* * * * *